(12) United States Patent
Marasco et al.

(10) Patent No.: US 7,186,697 B2
(45) Date of Patent: Mar. 6, 2007

(54) NUCLEIC ACID DELIVERY SYSTEM, METHODS OF SYNTHESIS AND USE THEREOF

(75) Inventors: Wayne A. Marasco, Wellesley, MA (US); Si-Yi Chen, Brookline, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 0 days.

(21) Appl. No.: 08/822,033

(22) Filed: Mar. 24, 1997

(65) Prior Publication Data

US 2004/0023902 A1 Feb. 5, 2004

Related U.S. Application Data

(63) Continuation of application No. 08/199,070, filed on Feb. 22, 1994, now abandoned.

(51) Int. Cl.
| | |
|---|---|
| *A61K 31/70* | (2006.01) |
| *A61K 39/395* | (2006.01) |
| *C07H 21/02* | (2006.01) |
| *C07H 21/04* | (2006.01) |
| *C07K 1/00* | (2006.01) |

(52) U.S. Cl. .................... 514/44; 536/23.4; 536/23.53; 530/350; 530/402; 424/178.1

(58) Field of Classification Search .................... 514/2, 514/44; 530/387.1, 350, 358, 387.3; 536/23.1, 536/23.4, 23.5, 23.7, 24.1; 435/172.3, 69.1
See application file for complete search history.

(56) References Cited

U.S. PATENT DOCUMENTS 5,166,320 A * 11/1992 Wu et al. .................... 530/395

FOREIGN PATENT DOCUMENTS

| CA | 2012311 | * | 9/1990 |
|---|---|---|---|
| WO | WO92/22332 | | 12/1992 |
| WO | WO93/04701 | | 3/1993 |
| WO | WO94/02610 | | 2/1994 |
| WO | WO94/04696 | | 3/1994 |

OTHER PUBLICATIONS

DT Curiel et al (1991) Proc Natl Acad Sci USA. 88:8850-8854.*
VK Chaud havy et al (1990) Proc Natl Acad Sci USA 87: 1066-1070.*
K Ryder et al (1989) Proc Natl Acad Sci USA 86: 1500-1503.*
Chen, S.Y., et al., Gene Therapy, vol. 2 No. 116-123 (Mar. 2, 1995).
Kabanov, A., et al., Journal of Controlled Release 28:15-35 (Jan. 1994).

* cited by examiner

*Primary Examiner*—Joseph Woitach
(74) *Attorney, Agent, or Firm*—Nixon Peabody LLP; Ronald I. Eisenstein; Leena H. Karttunen

(57) ABSTRACT

A nucleic acid delivery system is described. The delivery system contains a fusion protein having a target moiety and a nucleic acid binding moiety, and a nucleic acid sequence bound to the nucleic acid binding moiety of the fusion protein. The target moiety can be an antibody or a ligand. The use of this nucleic acid delivery system to transienntly or stably express a desired nucleic acid sequence in a cell is disclosed. Also disclosed is the use of this delivery system to target a cell and deliver a desired product.

18 Claims, 12 Drawing Sheets

Gene Therapy Form of Immunotoxins

FIGURE 1

Basic region                              Leucine zipper

GCN4-bZIP1: | PESSDPAALKRARNTEAARRSRARKLQRMKQ | LEDKVEELLSKNYHLENEVARLKKLVGER

GCN4-br1:   | PESSDPAALKRARNTEAARRSRARKLQRMKQ | GGC-NH$_2$

FIGRUE 13

| | | | | |
|---|---|---|---|---|
| Human FMR1 (1) | 222 QFIVREDLNG | LAIGTHGANI | QQARKVPGVT | |
| Human FMR1 (2) | 145 VHQVPRNLVG | KVIGKNGKLI | QEIVDKSGVV | |
| Yeast HX (3) | 228 VINVPAEHVP | RIIGHNGDNI | NDIRAEYGVE | |
| E. coli RP S3 | 64 RVTIHTARPG | IVIGKKGEDV | EKLRKVVADI | |
| Yeast MER1 | 181 EIKINKTQIT | FLIGAKGTRL | ESLREKSGAS | |
| E. coli PNP | 337 TIKINPDKIK | DVIGHGSVI | RAITEETGTT | |
| Human hnRNP K (1) | 46 RILIQSKNAG | AVIGKGKNI | KAIRTDYNAS | |
| S. acidocaldarius YRP3 (1) | 23 IILINPESIG | VAIGKNGLNV | RKIEKLINKS | |
| Chicken VIG (8) | 657 EVSIPSKLHN | SIIGAKGRFI | RSIMEECGGV | |
| M. vannielii YRP7 (2) | 103 YIRVHPRLRR | AIIGDKGKNI | DRAVDIAGRL | |
| Human RP S3 | 47 EIIILATRTQ | NVLGEKGRRI | REITAVVQKR | |
| Consensus | -I-I--f-I- | -VIGKNGfNI | ffLRf--G-- | |
| | V V | V L | DV I | |
| | L | M I | A | |
| | | ↓ | | |
| | | I304 → N FMR1 missense | | |

FIGURE 14

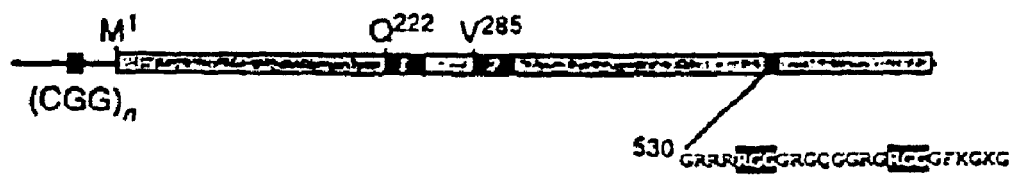

FIGURE 15

NUCLEIC ACID DELIVERY SYSTEM, METHODS OF SYNTHESIS AND USE THEREOF

This application is a continuation of application Ser. No. 08/199,070 filed on Feb. 22, 1994 now abandoned.

In recent years, a new form of therapy, gene therapy, has been proposed to treat a variety of maladies including cystic fibrosis (CF) [Rosenfeld, M. A., et al., *Cell* 68:143–155 (1992); Rosenfeld, M. A., et al., *Science* 252:431–434 (1991), Ferkol, T., et al., *J. Clin. Invest.* 92:2394–2400 (1993)], tumors such as retinoblastoma, diseases caused by infection by a virus such as the human immunodeficiency virus (HIV), for example HIV-1 infection [Baltimore, D., *Nature* 335, 395–396 (1988)], etc. In this form of therapy, a gene is introduced into cells so that the cells will express that gene. The gene can positively potentiate the cells, e.g., supply a missing protein, stimulate the immune system, or it may act in a negative manner, for instance expressing a viral inhibitor, which can result in the inhibition of the virus such as HIV-1 replication and thus infection. Several approaches including anti-sense RNA, ribozymes and dominant-negative mutants have been shown to be able to inhibit HIV-1 infection at the cellular level [Hasseloff, J, et al., *Nature* 334:585–591 (1988); Von der Krol, A. R., et al., *BioTechniques* 6:958–976 (1988); Malim, M. H., et al., *Cell* 58:205–214 (1989); Trono, D., et al., *Cell* 59:113–120 (1989); Sullenger, B., et al., *Cell* 63:601–608 (1990); Green, G., et al., *Cell* 58:215–223 (1989); Buonocore, L., et al., *Nature* 345:625–628 (1990)]. The intracellular delivery and expression of a human antibody, such as an anti-gp120 single chain antibody, is able to inhibit viral replication, etc. For example, the anti-gp120 antibody inhibits HIV-1 envelope glycoprotein maturation and function [Marasco, W. A., et al., PCT Application No. PCT/US93/06735, filed July 1993].

However, despite these advances, a major impediment to the development of gene therapy protocols for treatment and prevention of malignancies, diseases, etc. using any of these strategies is the relatively inefficient means to effectively transduce the desired genes into the desired target cells. Although murine retroviral vectors have been widely used to transfer gene into cells, they indiscriminately infect many cell types and limitedly infect desired targeted cells. In addition, retroviral vectors contain potentially hazardous viral DNA along with therapeutic genes. Therefore, these vectors may not be optimal as an efficient transfer system for the human gene therapy of, for instance, AIDS [Miller, A. D., *Nature* 357:455–46 (1992); Eglitis, M. A., et al. *Science* 230:1395–1398 (1985); Dizerzak, E. A., et al., *Nature* 331: 35–41 (1988)]. To resolve the problem of specific delivery for HIV infected cells, defective HIV vectors which can specifically transfer a gene into HIV susceptible cells have been developed. [Poznansky, M., et al., *J. Virol.* 65:532–536 (1991); Shimada, T., et al., *J. Clin. Invest.* 88:1043–1047 (1991)]. However, this approach may not be practical with all viruses and malignancies. Further, the theoretical potential of recombinant rescue of the defective vector, however low, may impede its use.

The delivery and expression of a recombinant gene into cells has also been achieved using liposomes, lipofectin, and calcium phosphate-precipitated methods either in vitro or in vivo [Nicolau, C., et al., *Proc. Natl. Acad. Sci. USA* 80:1068–1072 (1983); Brigham, K. L, et al., *Am. J. Med. Sci.* 298:278–281 (1989); Nabel, E. G., et al. *Science* 249: 1285–1288 (1990); Benvenisty, N. et al., *Proc. Natl. Acad. Sci. USA* 83:9551–9555 (1986); Chen, S. -Y., et al., *J. Virol.* 65:5902–5909 (1991)]. These methods have several advantages over retroviral systems for gene therapy. Plasmid DNA constructs containing suitable promoter elements are technically easier and less time consuming to prepare and test than retroviral vectors. Plasmid DNAs are more suitable for large-scale preparation than are the infections retroviruses. Plasmid DNAs can also permit the delivery of larger-sized segments of DNA than is possible with retrovirus-based systems. One additional advantage is that plasmid DNA may exclude deleterious side effects of retroviral vectors such as virus infection or cancer in a small percentage of patients. However, the potential for delivery of genes in vivo using these methods is limited by a lack of cell specificity and efficiency.

In an attempt to overcome the problem of cell-specific gene transfer, Wu and Wu, *J. Biol. Chem.* 262:4429–4432 (1987) have proposed a chemically coupled receptor-mediated gene transfer system which uses receptor-mediated endocytosis to carry DNA or RNA molecule into target hepatocytes or primary hematopoietic cells. The strategy of this system is based on the fact that such cells possess unique astalglycoprotein receptors on their surface that bind and internalize asialoglycoproteins, its ligand. The proteins (ligands) are preferably coupled to poly-L-lysine which can bind DNA or RNA to form soluble complexes by a strong, electrostatic interaction. This system has been reported to transfer genes into the targeted hepatocytes or primary hematopoietic cells at the cellular level as well as in animal studies [Wu, G. Y., et al., *J. Bio. Chem.* 263:14621–14624 (1988); Zenke, M., et al., *Proc. Natl. Acad. Sci.* 87:3655–3659 (1990); Wu, C. Y., et al., *J. Biol. Chem.* 266:14338–14342 (1991); Curiel, D. T., et al., *Proc. Natl. Acad. Sci. USA* 88:8850–8854 (1991); Wagner, E. et al., *Proc. Natl. Acad. Sci. USA* 87:3410–3414 (1990); Curiel, D. T., et al., *Human Gene Therapy* 2:230–238 (1992)]. However, the overall efficiency of this method has been reported to be relatively low because endocytosis is relatively inefficient in that the DNA frequently does not get out of the endosomial compartment and is ultimately degraded in lysosomes. Thus, multiple administrations are necessary and antigenicity of this system can be a problem. Furthermore, the synthesis of the delivery system is relatively time consuming as one has to first couple the poly-L-lysine to the asialoglycoprotein and then subsequently couple the ligand-polylysine complex to the exogenous DNA. Furthermore, in its typical application, the exogenous DNA introduced into the cell is not presented in a manner which is stably incorporated into the chromosome. Thus, expression is transient. Accordingly, repeated administration is necessary for this reason also. However, as mentioned the polylysine moiety as an artificial moiety may trigger an antigenic reaction limiting the ability to repeatedly use this system.

Another form of therapy that has been proposed is delivering an already expressed protein to the target cell. In one common form of cancer therapy, one introduces cytopathic or cytotoxic agents to the malignant cells in order to kill them. However, care must, be taken to minimize the harm to healthy tissues and cells. Thus, strategies have been developed to try to specifically target the unhealthy cells. The use of immunotoxins is one method of such therapy. An inmunotoxin is a class of cytotoxic agents consisting of a toxin protein linked to a monoclonal antibody or a ligand, which binds specifically to a target on the cell surface [Vitetta, E. S., et al. *Science* 238:1098 (1987); Pastan, I., et al., *Cell* 47:641 (1986); Pastan, I., et al., *Science* 254:1173 (1992)]. Due to the predicted specificity for the cell and the potential for efficacy, this therapy has been predicted to play an important role in therapy against cancer and various diseases. However, in practice this has not proven to be the case, Rather, the toxins are highly antigenic proteins. Neutralizing antibodies against these toxins typically arise within two weeks after the first exposure, severely limiting their effectiveness after only one or two therapy sessions. Thus, strategies, such as use of immunosuppressive agents to suppress immune reaction have been proposed. However, this is not only difficult to achieve, but may not be beneficial to the ultimate outcome of the therapy, since the immune system cannot then perform its function such as fighting infection, other tumor cells and pathogens.

Accordingly, it would be desirable to have a nucleic acid delivery agent that can be assembled more simply than other nucleic acid delivery systems, such as the delivery system of Wu and Wu.

It would also be desirable if such a delivery system could be synthesized more readily than is possible with a chemical coupling process.

It would also be desirable that the nucleic acid delivery system could readily be adapted to be used to specifically target a variety of target cells It would also be desirable if the delivery system had lower antigenicity than many currently available delivery systems. For example, it would be desired if it could be used to deliver a cytotoxic agent, e.g. an immunotoxin, to a cell without the antigenicity currently associated with such systems.

It would also be beneficial if this system did not have the potential of causing disease on its own by malignant transformation of a cell such as can occur with viral delivery systems.

SUMMARY OF INVENTION

We have now developed a highly efficient nucleic acid delivery system to a desired target cell. This system can be used, for example, to deliver a gene coding for the essential portion of a toxin protein. The nucleic acid, either DNA or RNA, is coupled to a fusion protein. The fusion protein consists of a target moiety and a nucleic acid binding moiety, for example a DNA binding moiety. For example, the target moiety preferably can be an antibody, more preferably a single chain antibody, a Fab portion of the antibody or a (Fab')$_2$ segment. If the target animal is a human, the DNA binding moiety should preferably be a human DNA binding moiety, such as protamine.

BRIEF DESCRIPTION OF THE DRAWINGS

Figure 1:
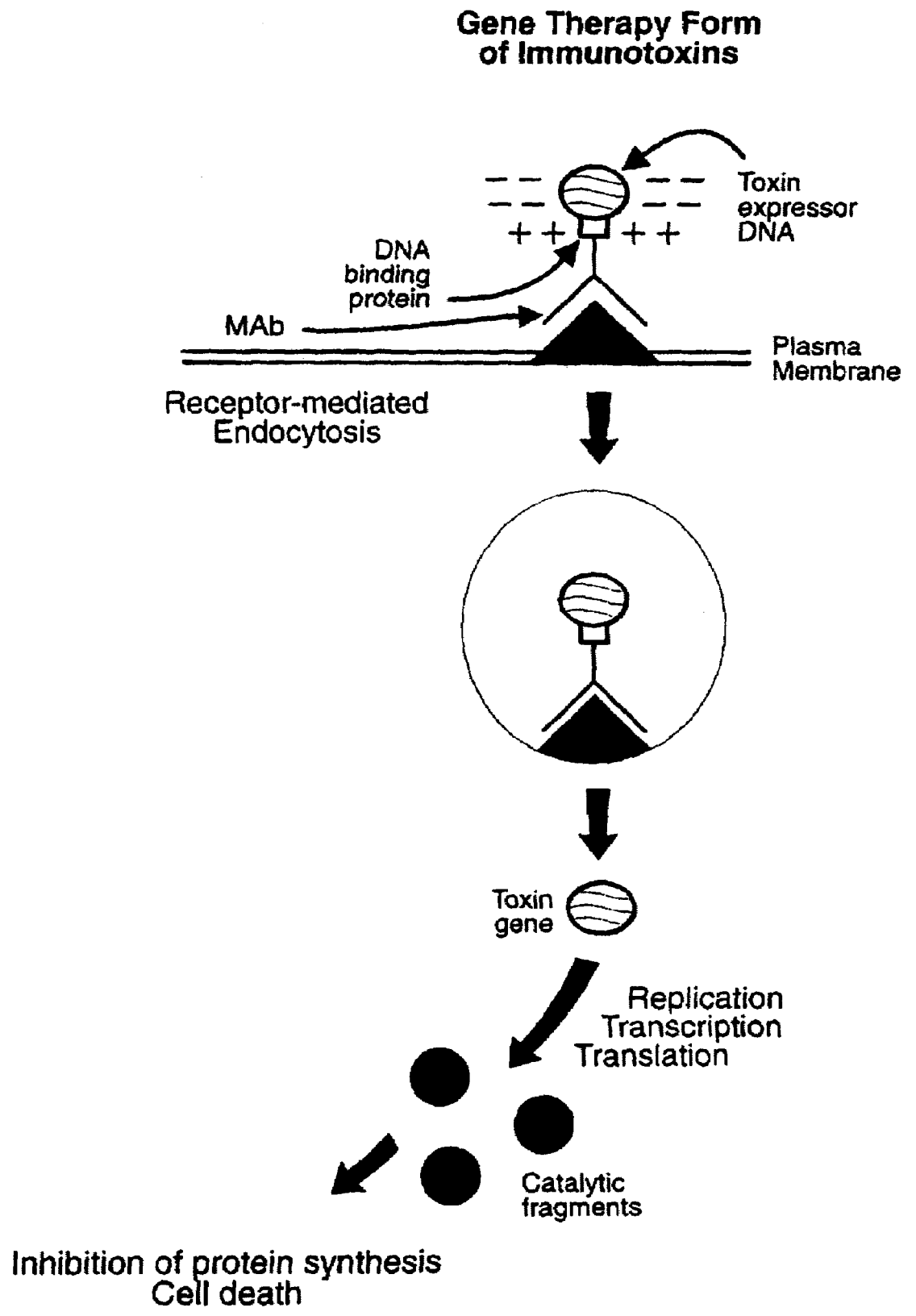

FIG. 1 is a schematic representation of one embodiment of the use of nucleic acid delivery system according to the present invention.

FIG. 13 is a reproduction of FIG. 1 of Talanian, et al., *Science* 249:769–771 (1990).

FIG. 14 is a reproduction of FIG. 1A of Ashley, et al., *Science* 262:563–566.

FIG. 15 is a reproduction of FIG. 1B of Ashley, et al., supra.

DETAILED DESCRIPTION OF THE INVENTION

Figure 2:
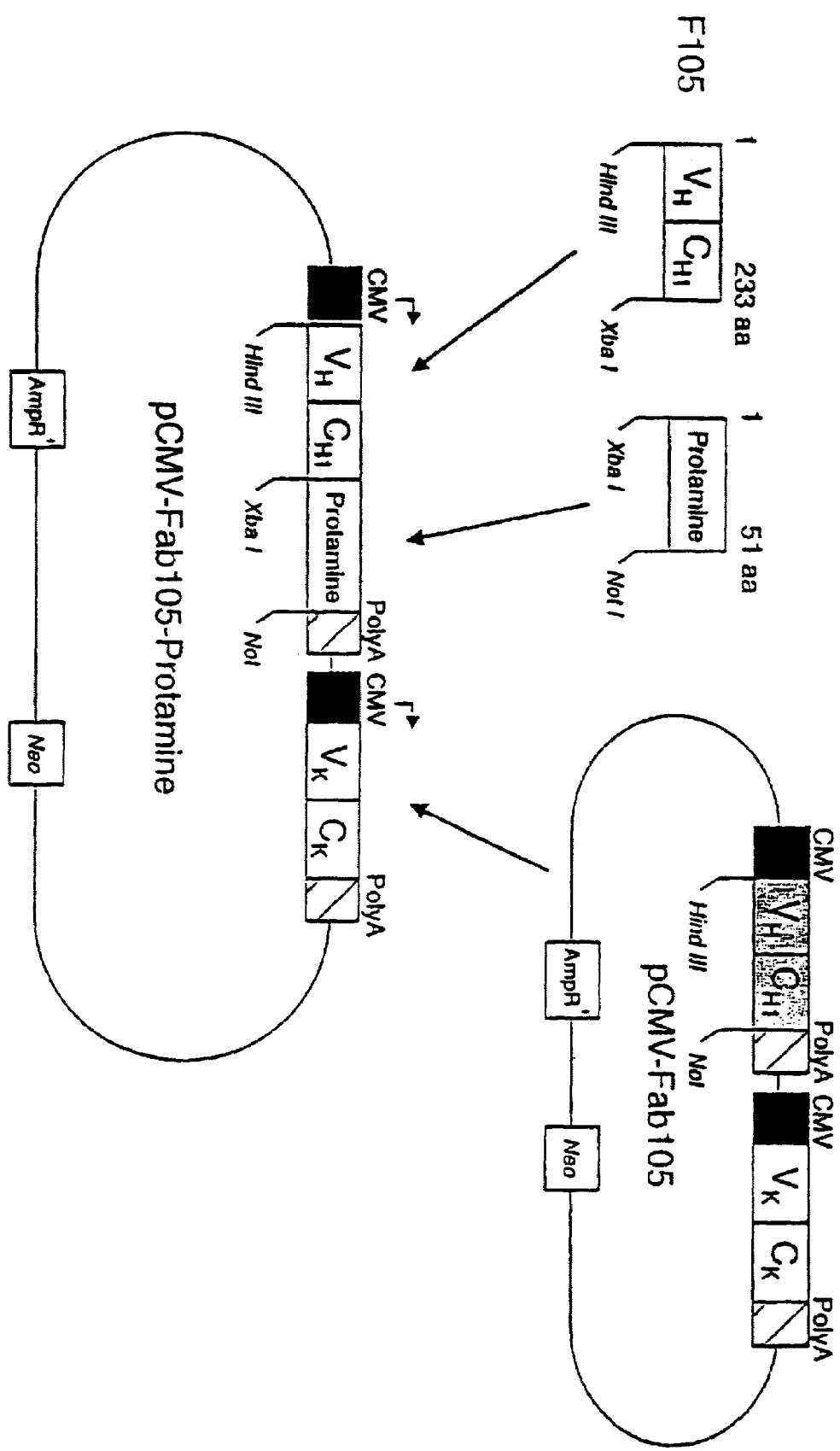
FIG. 2 is a schematic representation of one embodiment of the expression vector for the fusion protein. It is a schematic representation of a bi-cistronic mammalian expression vector, which will encode an antibody for the HIV gp120 protein fused to a protamine protein.

We disclose herein a new nucleic acid delivery system. The system comprises a fusion protein which binds the desired nucleic acid sequence.

The fusion protein comprises a target moiety and a binding moiety. The target moiety is preferably a protein that will specifically bind to a site on the target cell. For example, it can be a ligand for a ligand specific receptor for instance a fibroblast growth factor receptor (FGF-R)) and the specific FGF for that receptor, e.g. basic FGF for a basic FGR-R. Alternatively, the protein can be an antibody specific to the target cells. For example, it can be an antibody to an HIV envelope protein, an antibody to an oncogenic determinant such as extracellular ligand-binding domain of an activated receptor, (e.g., erbB, kit, fms, neu ErbB2), etc. It can also be an antibody to a receptor, for example, an antibody to the GM-CSF receptor. Preferably, the target moiety is an antibody. Still more preferably, the antibody is a single chain antibody comprising the binding sequence of the antibody, a (Fab')$_2$ segment or the Fab fragment of the antibody. More preferably the antibody is a single chain antibody or a (Fab')$_2$ segment.

The particular target moiety chosen can be determined empirically based upon the present disclosure depending upon the target cell. For example, with somatic cell therapy or in vivo with readily accessible cells or tissues such as an intravascular target, the important attributes of the target moiety are affinity and selectivity. In such instances the use of single chain antibodies as the target moiety is preferable. However, when the target cell is not readily accessible, such as when the cell is part of a large solid tumor mass with a poor blood supply and high interstitial pressure, the serum half—life is extremely important to consider. In such instances, the full antibody and (Fab')$_2$ segments are typically preferred. In a preferred embodiment, one could synthesize the fusion protein so that the binding moiety is attached to the carboxy terminus of an intact immunoglobulin such as IgG$_1$.

In order to limit antigenic reaction, the targeting moiety is preferably selected to take into account the host animal whose cells will be targeted. Thus, if the target animal is a mouse, one preferably uses murine antibodies, whereas if the target animal is a human, one preferably uses a human antibody or a humanized antibody.

The second part of the fusion protein consists of a nucleic acid binding moiety, either a DNA or RNA binding moiety. Preferably, one uses a moiety that can bind either DNA or RNA. This binding moiety can be any protein from the target animal that will bind either DNA or RNA. For example, it can be protamine, which is a small basic DNA binding protein, which serves to condense the animal's genomic DNA for packaging into the restrictive volume of a sperm head [Warrant, R. W., et al., *Nature* 271:130–135 (1978); Krawetz, S. A., et al., *Genomics* 5:639–645 (1989)]. The positive charges of the protamine can strongly interact with negative charges of the phosphate backbone of nucleic acid, such as DNA resulting in a neutral and stable DNA—protamine complex. The nucleic acid can be either DNA or RNA depending on the purpose. For example, the nucleic acid to be transferred can be used to express an antibody intracellularly, dominant negative mutants, anti-sense RNA, ribozymes or a cytotoxic agent. For example, the cytotoxic agent can be a portion of a bacteria or plant toxin which is extremely potent such as ricin, the catalytic fragment of *Pseudomonas exotoxin* A (PEA), etc.

The nucleic acid can be used for transient or table transfection of the cell. For example, when the nucleic acid encodes a factor which is lethal to the cell such as a DNA segment encoding a toxin, transient expression is sufficient. In contrast, where it expresses a factor such as a suppressor gene (e.g. retinoblastoma), or a protein that is not being expressed at sufficient levels, e.g. adenosine deaminase (ADA) [Belmont, J. W., et al., *Mol. & Cell. Biol.* 8:5116–5125 (1988); Palmer, T. D., et al., *Proc. Natl. Acad. Sci USA:*1055–1059 (1987), uridine diphosphate (UDP)-glucuronyl-transferase [Ponder, K. P., et al., *Proc. Natl. Acad. Sci USA* 88:1217–1221 (1991)], or insulin, stable integration into the cells chromosome may be desired. In those instances where stable integration is desired the nucleic acid can be a DNA segment wherein the gene coding for the desired factor is inserted into a cassette that will facilitate integration into the cell. For instance, the integration cassette which surrounds the gene can be a 5' and 3' LTR (long terminal repeat) of a retrovirus i.e. MMLV, an ITR (inverted terminal repeat unit, i.e. adeno associated virus), etc. [See, e.g., Scherdin, U., et al., *J. Virol,* 64:907–912 (1990); Stief, A., et al., *Nature* 341:343–345 (1989); Phi-Van, L., et al., *Mol. & Cell. Biol.* 10:2302–2307 (1990); Phi-Van, L. et al., *The EMBO Journal* 7:655–664 (1988)]. This cassette can be prepared by standard techniques. For example, mammalian expression vectors where a gene of interest can be inserted between LTRs or ITRS. One can construct a cassette containing flanking LTR or ITR regions at both ends, a promoter/enhancer, preferably with a polylinker for the gene of interest to be inserted in between, and when desired a selectable marker based upon the present disclosure using known techniques. This cassette with the desired nucleic acid, e.g. gene or genes, of interest is the nucleic acid segment.

The target moiety specifically brings the delivery system to the target cell.

One can also use localization sequences to intracellularly deliver the released RNA or DNA to a cellular site of interest.

Thereafter, the targeted cell can internalize the delivery system, which is bound to the cell. Typically, the delivery system binds to a specific receptor on the cell.

For example, membrane proteins on the cell surface, including receptors and antigens can be internalized by receptor mediated endocytosis after interaction with the ligand to the receptor or antibodies. [Dautry-Varsat, A., et al., *Sci. Am.* 250:52–58 (1984)]. This endocytic process is exploited by the present delivery system. Because this process can damage the DNA or RNA as it is being internalized, it is preferable to include a strong promoter for the nucleic acid that is to be expressed. Similarly, the use of a segment containing multiple repeats of the gene of interest may be desirable. One can also include sequences or moieties that disrupt endosomes and lysosomes. see, e.g., Cristiano, R. J., et al., *Proc. Natl. Acad. Sci. USA* 90:11548–11552 (1993); Wagner, E., et al., *Proc. Natl. Acad. Sci. USA* 89:6099–6103 (1992); Cotten, M., et al., *Proc. Natl. Acad. Sci. USA* 89:6094–6098 (1992).

In deciding what type of nucleic acid segment to use, the skilled artisan will take into account the protein being expressed in light of the present specification. For example, when one is introducing a toxin protein, because of its extreme cytotoxicity, the expression of only a few molecules are needed to kill a cell. In other cases such as with expressing ADA, larger amounts of protein expression are needed and the use of LTRs, ITRs, as part of the DNA cassette, and/or lysosomal disrupting agents such as replication-defective adenoviruses may be used.

The particular protein chosen for the targeting moiety will depend upon the target cell. For example, if one is targeting an infected cell, such as an HIV infected cell, one can use a monoclonal antibody that will specifically target HIV infected cells. This would include an antibody against the envelope glycoprotein. One can use any of a number of known antibodies against HIV-1 gp120 or HIV-2 gp120, such as 15e, 21h [Thali, M., et al., *J. Virol.* 67:3978–3988 (1993)], F105, 176 and 48d. If one wants to deliver the nucleic acid sequence prophylactically such as a gene for intracellular expression of an antibody, a decoy sequence, etc., one can target highly susceptible cells by targeting receptors present on such cells such as the CD4 receptor for HIV susceptible cells. In such a situation, the protein can be a ligand that will preferentially bind to the receptor, for example, CD4, as well as using an antibody to the receptor, such as an antibody to the CD4 receptor.

This strategy for choosing the targeting moiety is very adaptable. For example, certain tumors are frequently associated with cells possessing a large amount of a particular cell surface receptor (e.g. neu with breast cancers), or an abnormal form of a particular protein.

Other receptors of interest include those for lymphokines such as interleukins and interferons, for example, the interleukin-2 (IL-2) receptor (IL-2R). The p55, IL-2R α chain also referred to as the Tac protein is associated with Ag or mitogen-activated T-cells but not resting T-cells. It is expressed in high levels on malignant cells of lymphoid cancers such as adult T-cell leukemia, cutaneous T-cell lymphoma and Hodgkins disease. The anti-Tac antibody will bind to this protein. Humanized version of such antibodies are known and described in Queen, C., et al., *Proc. Natl. Acad. Sci. USA:*10029–10039 (1989); Hakimi, J., et al., *J. of*

*Immun.* 151:1075–1085 (1993) (Mikβ1 which is a Mab against IL-2R β chain); Kreitman, R. J., et al., *J. of Immun.* 149:2810–2815 (1992); Hakimi, J., et al., *J. of Immun.* 147:1352–1359 (1991).

Antibodies to these various proteins are known and available. These antibodies can readily be adapted for use in this system by following the general procedures described herein, and substituting the gene coding for the desired binding site for the exemplified gene. For example, where the targeted cell is an HIV-infected cell, the targeting moiety can target the HIV envelope glycoprotein. Any number of antibodies to this protein can be used. For instance, a recombinant antibody based on the F105 antibody is made by known teachings techniques. [Posner, M. R., et al., *J. Immunol.* 146:4325–4332 (1991); Thali, M., et al, *J. Virol.* 65:6188–6193 (1991); Marasco, W. A., et al., *Proc. Natl. Acad, Sci. USA* 90:7889–7893 (1993)] other antibodies that can be made include, 15e, 21h, 17b, 48d, etc.

A vector for expression of the antibody can be made as described herein. For example, a bicistronic mammalian expression vector which will express the Fd portion of the antibody ($V_H$ and $C_H$) and the binding region of the light chain (e.g. a kappa chain) of, for example, the F105 antibody can be constructed by using an Fd fragment without a stop codon and amplifying the segment by standard techniques, for example by polymerase chain reaction (PCR). The upstream primer preferably wil correspond to the leader sequence of the immunoglobulin of the animal from which the cells of the delivery agent is to be used (for example, where the target cell is a human cell a human immunoglobulin of amino acids 1–6), with an additional convenient cloning site such as a HindIII site. The downstream primer can correspond to amino acids by the carboxy terminus of the heavy chain constant region. For example, with an antibody based upon F105, amino acids 226–233 of human heavy chain CHI domain with a convenient cloning site inserted, such as the XbaI site. The PCR reaction is performed according to standard means. By this means the gene or gene segment encoding the targeting moiety of the fusion protein is prepared.

As described above, the second portion of the fusion protein is the binding moiety. Preferably, one uses a single vector containing gene segments that will express both the targeting moiety and the binding moiety. However, one can use a vector system to co-transfect a cell with at least two vectors and select for cells expressing the fusion protein. Preferably, one uses a single vector. One preferably attaches the sequence encoding the target moiety to a gene, or gene segment, encoding the binding moiety by standard means. For example, a gene for human protamine [Balhorn, *J. of Cell. Biol.* 93:298–305 (1982)]. Other nucleic acid binding proteins include GCN4, Fos and Jun which bind DNA through a common structural motif consisting of several basic residues and an adjacent region of about 30 residues containing a heptad repeat of leucines, the "leucine zipper" that mediates dimerization [Talanian, R. V., et al., *Science* 249:769–771 (1990) Talanian, et al. state at 769:

> This "bZIP" (4) [4. C. R. Vinson, P. B. Sigler, S. L. McKnight, Science 246, 911 (1989)] motif consists of a region with several basic residues that probably contacts DNA directly and an adjacent region of about 30 residues containing a heptad repeat of leucines, the "leucine zipper" (5) [5. W. H. Landschultz, P. B. Sigler, S. L. McKnight, ibid. 240, 911 (1989)], that mediates dimerization. Such bZIP dimers bind DNA sites that are approximately diad-symmetric (3) [Reviewed by P. F. Johnson and S. L. McKnight, *Annu. Rev. Biochem.* 58, 799 (1989); K. Struhl, *Trends Biochem. Sci.* 14, 137 (1989)].

and later:

> A peptide (GCN4-brl), corresponding to residues 222 to 252 of GCN4 (22) [22. G. Thireos, M. D. Penn, H. Greer, *Proc. Natl. Acad. Sci. U.S.A.*, 81, 5097 (1984); A. G. Hinnebusch, ibid., p. 6442.], was synthesized (23) [Peptides were synthesized on an Applied biosystems Model 430A peptide synthesizer with standard reaction cycles modified to include acetic anhydride capping. Peptides were cleaved from the resins by low-high HF cleavage (Immunodynamics, Inc., San Diego, Calif.) and desalted by Sephadex G-10 chromatography in 5% acetic acid. Purifications were by high-performance liquid chormatography with a Vydac reversephase $C_{18}$ column and a linear gradient of $CH_3CN$—$H_2O$ with 0.1% trifluoroacetic acid. Fast atom bombardment mass spectrometry; GCN4-brl: calculated, 3796.5; found, 3795.8; GCN4-bZIPl: calculated, 7015.4 found, 7015.5.]with a Gly-Gly-Cys linker (6) [6. E. K. O'Shea, R. Rutkowski, P. S. Kim, ibid. 243, 538 (1989)] added at the carboxyl terminus (FIG. 1). The glycines were included to provide a flexible linker in the disulfide-bonded dimer, referred to as GCN4-brl$^{ss''}$. The peptide was made as the carboxyl-terminal amide to avoid introduction of additional charge. A second peptide (GCN4-bZIPl), corresponding to the entire bZIP region of GCN4 (residues 222 to 281), was also synthesized (FIG. 1). This 60-residue peptide is capable of dimerization and sequence-specific DNA binding (8) [8. I. A. Hope and K. Struhl, *Cell* 46, 885 (1986)]. FIG. 1 at 769 states:

> Sequences of the peptides studied (23) [23. Peptides were synthesized on an Applied biosystems Model 430A peptide synthesizer with standard reaction cycles modified to include acetic anhydride capping. Peptides were cleaved from the resins by low-high HF cleavage (Immunodynamics, Inc., San Diego, Calif.) and desalted by Sephadex G-10 chromatography in 5% acetic acid. Purifications were by high-performance liquid chromatography with a Vydac reverse-phase $C_{18}$ column and a linear gradient of $CH_3CN$—$H_2O$ with 0.1% trifluoroacetic acid. Fast atom bombardment mass spectrometry; GCN4-brl: calculated, 3796.5; found, 3795.8; GCN4-bZIPl: calculated, 7015.4 found, 7015.5.]. GCN4-bZIPl consists of the 60 carboxyl-terminal residues of GCN4 (22). The leucines in the leucine repeat are underlined. GCN4-brl consists of the basic region residues (boxed) plus the carboxyl-terminal linker Gly-Gly-Cys. Abbreviations for the amino acid residues are: A, Ala; C, Cys; D, Asp; E, Glu; G, Gly; H, His; K, Lys; L, Leu; M, Met; N, Asn; P, Pro; Q, Gln; R, Arg; S, Ser; T, Thr; V, Val; and Y, Tyr.]; the TFIIS nucleic acid binding domain, which is seen in the C-terminal residues 231–280 [Qlan, X., et al., *Nature* 365:277–279 (1993)]; the ribonucleoprotein (RNP) family that is present in domains in human FMRI, the yeast protein HX, 14 domains of the chicken gene vigillin, merl, a yeast protein, bacterial polynucleotide phosphoylase, and the ribosomal protein S3 [Ashley, C. T., et al., *Science* 262:563–566] Ashley, et al. state in FIG. 1 at 563:

> Location and homologies of RNP family domains in FMRP. [FIG. 14] (A) Alignment (27) [27. M. Gribskov, R. Leuthy, D. Eisenberg, *Methods Enzymol.* 183, 146

(1989)]. The 12-residue element is not found in the sequence of *Drosophilia* HSF. It is possible that another element may serve the same function.] of the amino acid sequences that make up the KH domains of FMRP and several other proteins and the corresponding consensus sequence. Numbers in parentheses indicate the particular domain shown for the proteins that have multiple KH domains, and the number preceding the first residue indicates that position in the corresponding protein. Dark highlighting indicates similarities among all proteins, whereas stippled highlighting indicates similarity between the two KH domains of FMRP. Boldface residues show the positions of polar amino acids, indicated by if in the consensus sequence. The bracketed lysine (K) residues indicate this amino acid at either position in the domain. The position of the isoleucine-to-asparagine mutation at position 304 ($I^{304} \rightarrow N$) in a patient (6) [D. Wohrle, et al., *Am. J. Hum Genet.* 51, 299 (1992); A. K. Gideon, et al.. *Nature Genet.* 1, 341 (1992); K. De Boulle et al., ibid. 3, 31 (1993)] is indicated at the bottom. [FIG. 15] [1. W. T. Brown, *Am. J. Hum. Genet.* 47, 175 (1990); S. L. Sherman et al., *Ann. Hum. Genet.* 48, 21 (1984); 2. M. G. Butler, T. Mangrum, R. Gupta, D. N. Singh, *Clin. Genet.* 39, 347 (1991); 3. A. M. J. G. Verkerk, et al., *Cell* 65, 905 (1991); I. Oberle et al., *Science* 252, 1097 (1991); E. J. Kremer et al., ibid. p. 1711; A. Vincent et al, *Nature* 349, 624 (1991)]. (B) Diagram of FMRP [residue numbers are as described (7)]. [7. C. T. Ashley et al., *Nature Genet.* 4, 244 (1993)] The CGG repeat and initiating codon ($M^1$) are indicated as is each KH domain, labeled 1 and 2. Also shown is the amino acid sequence with the two RGG box domains highlighted. Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S. Ser; T, Thr; V, Val; W, Trp; and Y, Tyr.

Figure 16:
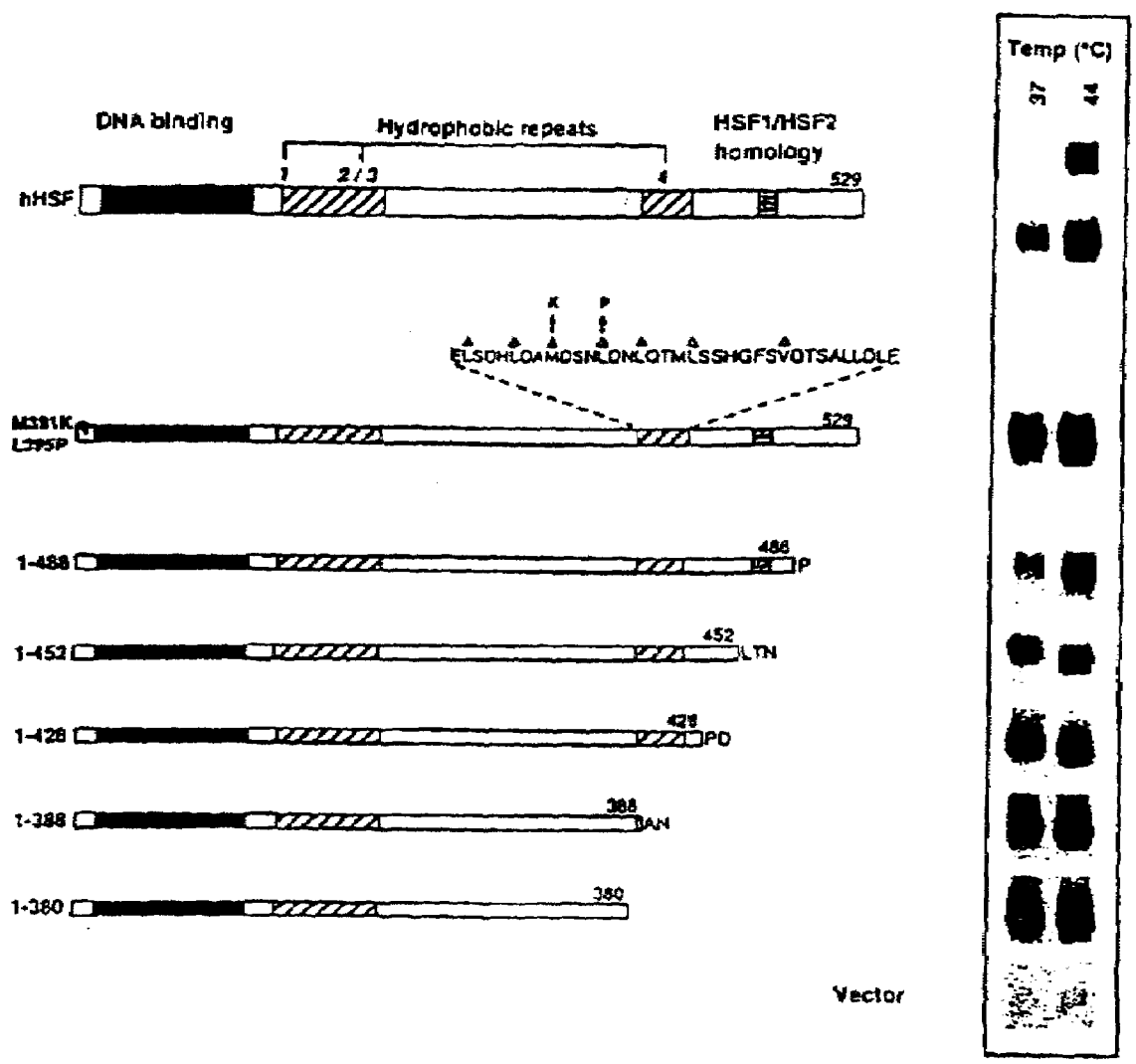
FIG. 16 is a reproduction of FIG. 1 of Rabindran, S. K., et al., *Science* 259:230–234 (1993).

FIGS. 1*a* and *b* are reproduced as FIGS. 14 and 15.; and the binding motifs in heat shock protein [Rabindran, S. K., et al., *Science* 259:230–234 (1993)] Rabitindran, et al., state in FIG. 1 at 231:

FIG. 1. [FIG. 16] Activity of wild-type and mutant human HSF1 proteins transiently expressed in 293 cells. Map of wild-type and mutant human HSF1 (hHSF) ORFs is at left. Numbers on the right indicate the end point of the truncated fragments; amino acids in the fourth hydrophobic repeat and appended by cloning at the COOH-terminal and are represented by the single-letter code (30). [30. Abbreviations for the amino acid residues are as follows: A, Ala; C, Cys; D, Asp; E, Glu; F, Phe; G, Glyp; H, His; I, Ile; K, Lys; L, Leu; M, Met; N, Asn; P, Pro; Q,. The host animal of the target cells will be used to determine which protein or protein fragment with a binding motif is used. For example, with a human host and for expression of human protamine one can use the known plasmid pTZ 19R-HP1 [Krawetz, S. A., et al. *Genomnics* 5:639–645 (1989)]. Preferably one would delete an intron in this gene so that the expression vector can also be used for expression of the fusion protein in prokaryotic systems as well as eukaryotic systems. PCR amplification would be performed by standard means. For example, using an upstream primer, which corresponds to sequences from the amino terminus, for example, corresponding to amino acids 1–6 of the protamine protein with a convenient restriction site, such as the XbaI cloning site and a downstream primer corresponding to the carboxy portion of the first exon, for example, amino acids 29–37 with additional sequences complimentary to the 5' amino acids in the second terminus (e.g. amino acids 38–40 in the second exon). A second PCR reaction can then be performed using the upstream primer corresponding to the amino terminus and the downstream primer corresponding to an overlapping portion to the carboxy terminus. For example, using a sequence corresponding to amino acids 31–40 with the sequence of amino acids 41 to the stop codon in the second exon and an additional convenient cloning site such as NotI. The first PCR amplified DNA segment can be used as a template. By using convenient restriction sites, one can cut out the targeting moiety and the binding moiety by known methods such as purifying them using standard techniques, e.g., agarose gel, For example, in the example described above, the PCR amplified Fd of F105 without a stop codon can be cut with HindIII/XbaI and purified by agarose gel. The PCR amplified protamine coding gene, without intron can be cut with XbaI/NotI and purified from agarose gel. The Fab105 plasmid can be cut with HindIII/NotI and the DNA segment purified from an agarose gel The HindIII/XbaI-cut Fd fragment and XbaI/NotI-cut protamine fragment can then be cloned into the HindIII/NotI sites of the plasmid containing F105 by three-piece ligation. See FIG. 2. The resulting expression vector thus contains a cartridge of an Fd-protamine fusion gene (inframe) and kappa-chain gene under the control of an independent promoter, such as a CMV promoter. The particular promoter that will be used depends upon the desired cell system for expression of the fusion protein. Promoters are known to the skilled artisan and can readily be selected based upon the present disclosure. For example, preferred promoters include CMV, SRα, RSV, MMLV LTR, SV40 and HIV-1 5' LTR.

This construct can readily be confirmed by standard means, such as DNA sequencing.

This expression vector can then be used to stably transform a cell line. The cell line can be any desired cell line including prokaryotic as well as eukaryotic cells. Preferred cell lines include mammalian cell including COS cells, kidney cell lines such as CHO, myeloma cell lines such as SP/0, and SP/2, HMMA2–11 TG10, and insect cell lines such as Drosophilla. Preferably, to reduce antigenicity one would use a mammalian cell line. More preferably, one would use a myeloma cell. Preferred cells include SP/0, SP/2, Sp2/0-Ag14, X63Ag8.653, FO, NSI/1-Ag4–1, NSO/1, FOX-NY, YB2/0 and 1R983F.

The transformation of the cell can be by any standard techniques. It is preferred that one stably transforms the cell, although in certain instances transient transformation by the DEAE-Dextran technique will be acceptable. Thus, one preferably uses a method for stably transforming the cell, such as the calcium phosphate precipitation method followed by selection of transformed cell lines such as by G418 selection. The transformed cell line can be cultured and the fusion protein harvested by standard techniques. For instance, the Fd-protamine protein and kappa-chain of F105 are expressed and secreted into the culture of COS transformed Fab105 protamine cells and detected by radiolabelling and immunoprecipitation with anti-human IgG antibody.

For example, a COST cell can be transfected with an expression vector containing the cartridge of the targeting moiety-binding moiety using lipofectin. Vectors include the vector pCMV-Fab105-protamine. The transfected cells can then be incubated in DMEM, supplemented with 10% fetal calf serum (FCS) for two days and replaced with a selection medium such as DMEM with 10% FCS and 500 μg G418. This is readily available, for example, from BRL. The G418 resistant colonies will appear after about two weeks and can be readily selected. Colonies can then be cloned with limiting dilution and examined by radiolabelling and immunoprecipitation, ELISA and immunofluorescent staining for expression of the recombinant fusion protein. The proteins can be secreted and purified in these cells by standard means. For example, the transformed COS cells can be grown in a flask with DMEM medium supplemented with 10% fetal calf serum and 500 μg/ml of neomycin. After reaching confluence, the cultures can be replaced with fresh DMEM without FCS every three days for two weeks. The collected culture mediums can be clarified by, for example, centrifugation at, for instance, at 500 rpm for 20 minutes at 4° C. and then concentrated using, for example, a membrane filter with a molecular weight cutoff of 10,000 dalton such as an Amico concentrator. The concentrated medium can then be loaded into an affinity column coupled with anti-human IgG kappa-chain monoclonal antibody, such as sold by Kirkegaard & Perry, Inc. The affinity column can be washed with PBS and loaded with the concentrated culture medium. The medium will then pass through the column, followed by PBS washings until no protein is detected in the eluate. The column is then washed with pre-elution buffer, for example, 10 mM phosphate at pH 8.0 and eluted from the column with 100 mN glycine at pH 2.4. The protein peak fractions are detected by standard means such as by for example Bradford protein assay (Biolab) and pooled together and dialyzed against 0.2 M NaCl.

In a preferred embodiment you would adapt the cell for growth in a serum-free medium. This can be done by the skilled artisan. For example, one can readily adapt COS and CHO cells. In doing this, relatively pure Fab-fusion proteins are secreted into the medium. Thus, the purification procedure is simpler.

The purified fusion protein is now ready to be combined with the desired nucleic acid sequence such as one for a positive potentiator (such as a gene for a cytokine, a gene for a missing or detective protein, etc.) or a sequence for a negative potentiator (such as a toxin, an anti-sense RNA, a suicide gene such as HSV thymidiac kinase, a ribozyme, a dominant-negative mutant, etc.). For example, when the nucleic acid encodes a toxin, one preferably takes care to alter the toxin gene to minimize its potential to affect non-targeted cells. This can be done by standard techniques such as deleting those sequences encoding recognition domains. Toxins are well known and include diphtheria toxin and truncated versions thereof, *pseudononas exotoxin*, and truncated versions thereof, Ricin/abrin, Blocked ricin/abrin, Ricin ToxinA-chain, ribosome inactivating protein, etc. All these proteins have different domains. For example, the gene encoding PEA has several domains: Domain I is responsible for cell recognition; Domain II for translocation of the toxin cross-membrane and Domain III for adenosine diphosphate (ADP)-ribosylation of elongation factor 2, which is the step actually responsible for cell death. [Gary, G. L., et al., *Proc. Natl. Acad. Sci. USA* 81:2645–2649 (1984); Allured, V. S., et al., *Proc. Natl. Acad. Sci. USA* 83:13220–1324 (1986); Siegall, C. B., et al., *J. Biol. Chem.* 264:14256–14261 (1989)]. Accordingly, by alterations in Domain I or Domain II, that render those domains incapable of expression, for example, by a frameshift mutation, insertion of termination sequences, or deletions one can minimize the ability of the toxin to affect neighboring cells. Thereafter, the skilled artisan can use standard techniques to insure that the other domains, or portions of domains where expression is desired, are used.

For example, as indicated above, with PEA only Domain III is absolutely required. However, we have found that including partial sequences from other domains makes the toxin more effective. For example, we prepared two PEA mammalian expression vectors. This is one in which Domain III (mature PEA amino acid residues 405 to 613) only, referred to as pCMV-PEA III is expressed and one which encodes Domain III and partial Domain IB, a sequence of amino acids 385 to 613 (pcMV-PEAIbIII) is expressed. These sequences should be operably linked to a promoter which will permit expression in the target cell. For example, mammalian promoters such as CMV, SRα, RSV, SV40, MMLV LTR, HIV-1 5' LTR, are preferred. More preferably, CMV, HIV-1 5' LTR, RSV, and SV40. The toxin proteins encoded by these gene fragments lack a recognition domain. They are non-toxic to surrounding cells and are only toxic when expressed inside a cell. These expression vectors can readily be tested to determine how well they express a product intracellularly by a simple in vitro assay. For example, the expression of those DNA sequences encoding PEA toxin fragments can be tested by transforming a cell with the delivery system and observing the cytotoxicity of the cell. We have found that the pCMV-PEIbIII vector shows a higher level of ADP-ribosylation than the vector expression only Domain III and thus, we prefer using it.

FIG. 1 is a schematic representation showing the use of a nucleic acid delivery system according to the present system, wherein the nucleic acid sequence is a toxin expressor DNA.

In some instances, even with immunotoxins, resistant mutants can develop. In such instances, one can readily insert a different toxin gene or different types of nucleic acid segments into the nucleic acid cassette which is attached to the fusion protein. Thus, the present system permits the production and use of a wide range of DNA and RNA segments.

In some preferred embodiments one would administer a cocktail of nucleic acid delivery systems where the targeting moiety may be changed to broaden the number of targeted cells or alternatively the nucleic acid segment that is delivered is changed to widen the spectrum of products delivered to the target cell.

When the protein is a toxin, transient expression in the cell is all that is needed. However, when it is desired to stably transform a cell, the gene is placed into a cassette containing LTRs or ITRs at either side to foster stable integration. Alternatively the cassette can be an episomal vector such as one that contains an Epstein Barr virus for example, pEBV His A, B, and C, pREP4, pREP7, pREP10, which are sold commercially by Invitrogen Corporation.

The recombinant fusion proteins are combined with the nucleic acid segment by standard techniques. For example, the fusion protein can be mixed with given amounts of the desired nucleic acid sequence, either DNA or RNA, by known means such as mixing in solution. For example, in 0.2 M NaCl solution. The DNA or RNA is readily bound by the protamine. Thereafter, the carrier can be administered to the desired cell either for somatic cell therapy or used in vivo.

The delivery system can be delivered by any of a number of means. For example, it can be administered by parenteral injection (intramuscular (i.m.), intraperitoneal (i.p.), intravenous (i.v.) or subcutaneous (s.c.)), oral or other routes of administration well known in the art. Parenteral administration is preferred.

The amount used will typically be in the range of about 0.1 mg to about 10 mg/kg of body weight. The delivery system will preferably be formulated in a unit dosage form based upon the nucleic acid or nucleic acids being delivered.

For example, solid dose forms that can be used for oral administration include capsules, tablets, pills, powders and granules. In such solid dose forms, the active ingredient, i.e., targeting moiety, is mixed with at least one inert carrier such as sucrose, lactose or starch. such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the antibody. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably, about 3 mg/ml to about 10 mg/ml.

Although receptor mediated gene delivery in certain embodiments may be relatively inefficient, by utilizing the present gene delivery system, one does not have to worry about antigenic reactions occurring from the use of higher dosages or repeated injections. This is because the targeting moiety and the DNA binding moiety can be designed so that they are either from the animal that one is injecting, such as a human, or made to be like that animal, i.e. using a humanized murine antibody or binding protein for a human. DNA itself is weakly or non-immunogenic. Thus, the entire agent is either non or weakly immunogenic. Since the delivery system can be efficiently produced and adapted to have high binding activity, it can be used repeatedly.

Additionally, as discussed above there are methods that can be utilized in the present system to improve the efficiency of the delivery system. For example, one can include targeting sequences such as nuclear targeting sequences associated with the nucleic acid segment to more efficiently deliver the nucleic acid to its desired target. Targeting sequences are known in the art and include for example, the nuclear localization signal on HIV gag p17 between positions 25 and 33 (SEQ ID NO:1) (KKKYYKLK). Thus, one can include a targeting sequence, preferably inside a liposome, as part of the fusion moiety to more effectively target the DNA.

The present invention is further illustrated by the following examples. These examples are provided to aid in the understanding of the invention and are not to be construed as a limitation thereof.

EXAMPLES

A bi-cistronic mammalian cell expression vector (pCMV-Fab105-Protamine) which contains a chimeric gene encoding the Fd of F105 fused to the human protamine protein in one expression cassette and the F105 kappa chain encoding gene in another expression cassette (FIG. 2) was constructed as follows.

Construction of Mammalian Expression Vector For Fab105-Protamine Fusion Protein

The pCMV-Fab105 plasmid was constructed as described below. This plasmid contains bi-cistronic expression cassettes for the Fd gene and kappa chain gene derived from F105 hybridonma. To construct a fusion protein expression vector, the Fd fragment of F105 without a stop codon was amplified by PCR using the pCMV-Fab105 as a template. The upstream primer (SEQ ID NO:2) (5'-TTTGAAT-TCAAGCTTACCATGGAACATCTGTGGTTC-3') corresponding to the leader sequence of human immunoglobulin of amino acids 1 to 6 with an additional HindIII cloning site (Kabat, et al., 1987), and the downstream primer (SEQ ID NO:3) (5'-GGTACCGAATTCTCTAGAACAA-GATTTGGGCTC-3') corresponding to the amino acids of 226 to 233 of human heavy chain constant region with an additional XbaI cloning site were used for PCR amplification. The PCR reaction was performed as described previously [Marasco, et al., *J. of Clin. Invest.* 90:1467–1478 (1992)].

The human protamine gene was amplified from the plasmid pTZ19R-HP1 [Krawetz, S. A., et al., *Genomics* 5:639–645 (1989)]. To delete an intron in the protamine gene in this clone (for expression in prokaryotic system as well), the first PCR amplification was performed using the upstream primer P1, (SEQ ID NO:4) (5'-GGTACCGAAT-TCTCTAGAATGGCCAGGTACAGATGC-3') which corresponds to the sequence of amino acids 1 to 6 of protamine protein with an additional XbaI cloning site, and the downstream primer (SEQ ID NO:5) (5'-TTTAGGATCCTTAA-CAACACCTCATGGCTCTCCTCCGTGTCTGGCAGC-3') which corresponds to amino acids 29 to 37 with additional sequence complementary to amino acids 38 to 40 in the second exon. The second PCR reaction was performed using the upstream primer P1 and the downstream primer, (SEQ ID NO:6) (5'-TTAATTGCGGCCGCTTAGTGTCT-TCTACATCTCGGTCTGTACCTGGCGCT-GACACCTCATGGCTCTCCTCCGTGTCTG3'), corresponding to amino acid sequence 31 to 40 with the sequence of amino acids 41 to stop codon in the second exon and an additional NotI cloning site. The first PCR-amplified DNA was used as a template.

To construct a bi-cistronic fusion protein expression vector, the PCR-amplified Fd of F105 without a stop codon was cut with HindIII/XbaI and purified from an agarose gel, The PCR-amplified entire protamine coding gene without intron was cut with XbaI/NotI and purified from an agarose gel. The pCMV-Fab105 plasmid was cut with HindIII/NotI and the DNA fragment about 7.0 kd was purified from an agarose gel. The HindIII/XbaI-cut Fd fragment and XbaI/NotI-cut protamine fragment were then cloned into the HindIII/NotI sites of pCMV-Fab105 by three-piece ligation. The resultant expression vector, designated as pCMV-Fab105-Protamine, contains Fd-protamine fusion gene (inframe) and kappa chain gene under the control of independent CMV promoter. This construct was confirmed by DNA sequencing.

The F105 Fd and human protamine DNA fragments which were cloned into the pCMV-Fab105 vector are shown in FIG. 2. The resulting bi-cistronic expression vector (pCMV-Fab105-Protamine) contains an expression cassette for the Fd105-Protamine fusion protein and another cassette for the kappa chain of F105.

A transformed mammalian cell line COS-Fab105-Protamine was generated after DNA transfection and G418 selection.

Construction of Transformed Cell Lines

To generate transformed cell lines, COS-1 cells were grown on 6-well plates and transfected with pCMV-Fab105-Protamine using lipofectin as described previously [Chen, S, -Y., et al., *J. Virol.* 65:5902–5909 (1991)]. The transfected cells were incubated in DMEM supplemented with 10% FCS for two days and replaced with selection medium (DMEM with 10% FCS and 500 µg/ml G418 (BRL). The G418 resistant colonies appeared after two to three weeks of selection. The colonies were subcloned with limited dilution and examined by radiolabelling and immunoprecipitation, ELISA, and imnmunofluorescent staining for expression of recombinant proteins as described [Marasco, W. A., et al., *Proc. Natl. Acad. Sci. USA* 90:7889 (1993)]. The Fd-protamine protein and kappa chain of F105 are expressed and secreted into the culture medium of COS-Fab105-Protamine cells as detected by radiolabelling and immunoprecipitation with anti-human IgG antibody See FIG. 3.

Purification of Fusion Proteins

The transformed COS cells (COS-Fab105-Protamine) were grown in flasks with DMEM medium supplemented with 10% fetal calf serum (FCS) and 500 µg/ml of neomycin. After reaching confluence, the cell cultures were replaced with fresh DMEM without FCS every three days for two weeks. The collected culture medium was clarified by centrifugation at 5000 rpm for 20 minutes at 4° C., and then concentrated using an Amico concentrator with membrane filter molecular weight cut-off 10,000 dalton. The concentrated medium was then loaded onto an affinity column coupled with anti-human IgG kappa chain monoclonal antibodies (Kirkegaard & Perry Inc.).

Preparation of the affinity column was made by mixing 2 mg of the purified monoclonal antibody with 1 ml of wet beads of protein A-sepharose CL-4B (Pharmacia Inc. Uppsala, Sweden) as described. Briefly, protein-A-sepharose 4B beads were washed with PBS and then mixed with purified antibodies in PBS at 4° C. overnight. The mixture was washed with 10 volumes of 0.2 M sodium borate (pH 9.0) and added with dimethypimelimidate to a final concentration of 20 mM. The mixture was stirred for 30 minutes at room temperature on a rocker, washed once with 0.2 M ethanolamine (pH 8.0) and then incubated for 2 hours at room temperature in 0.2 M ethanolamine on a rocker. After final washing, the beads coupled with antibodies were resuspended in PBS with 0.01% merthiolate.

The affinity column was washed with PBS, and loaded with the concentrated culture medium. The medium passed through the column followed with PBS washing until no protein was detected from the elute. The column was washed with pre-elution buffer (10 mM phosphate, pH 8.0) and eluted from the column with pH 2.4, 100 mN glycine. The protein peak fractions were detected by Bradford protein assay (Bio-Lab) and pooled together and dialyzed against 0.2 M NaCl. The DNA-binding portion of the fusion protein was examined by incubation of the DNA-cellulose with the culture medium of radiolabeled cells.

The transformed cell line (COS-Fab105-Protamine) was generated with G418 (Gibco-BRL) selection after transfection with pCMV-Fab105-Protamine DNA [Warrant, R. W., et al., *Nature* 271:130–135 (1978)]. The COS-Fab105 cell line was established as described previously [Warrant, R. W., *Nature* 271, supra]. To examine expressed proteins, the transformed cells were radiolabeled for 4 hours and precipitated with anti-human IgG (Southern Biotech) and protein A-Sepharose 4B beads or with DNA-cellulose (Pharmacia) and analyzed by SDS-PAGE as described previously [Chen,. S. -Y. et al., *J. Virol.* 65:5902–5909 (1991)]. To purify secreted Fab105-Protamine in the serum-free medium, the culture medium of COS-Fab105-Protamine cells is clarified, concentrated, and loaded onto an affinity column of Protein-A-sepharose 4B beads coupled with anti-human IgG monoclonal antibody, which was prepared according to described methods [Winter, G., et al., *Nature* 349:293–299 (1992)]. The bound-proteins on the column were eluted by 100 mM glycine (pH 7.5), and then concentrated and dialyzed against 0.20 M NaCl solution. For ELISA, microtiter plates were coated with recombinant gp120 (American Biotechnology Inc.) and incubated with known concentration of Fab105 or Fab105-Protamine proteins followed by incubation with anti-human IgG conjugated with alkaline phosphatase (Sigma) [Warrant, R. W., et al., *Nature* 271, supra].

Figure 3:
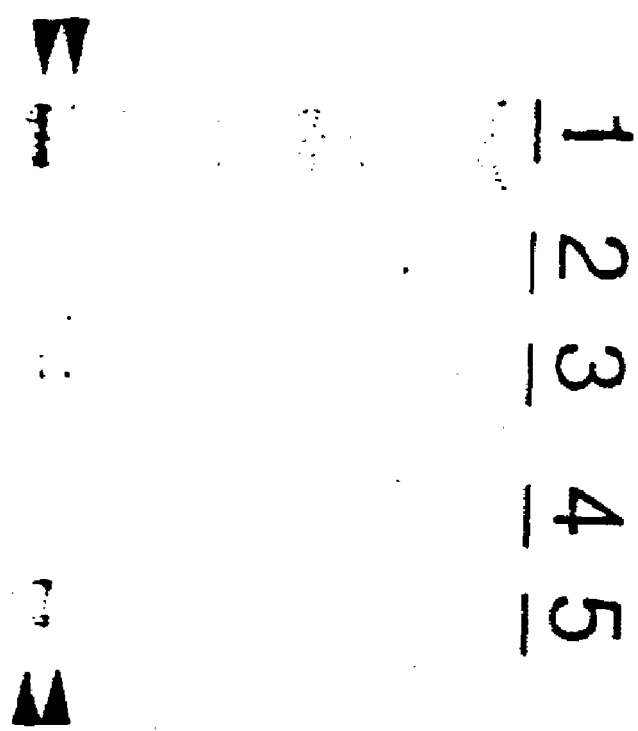
FIG. 3 is an autoradiograph showing radiolabeling and immunoprecipitation of expressed Fab105-protamine fusion proteins.

FIG. 3 shows radiolabeling and immunoprecipitation of the expressed fusion proteins. The transformed cell line (COS-Fab105-Protamine) was generated as discussed above. The cells on 6-well plates were continuously radiolabeled with $^{35}$S-cysteine for 4 hours and the culture medium of the cells was precipitated with either anti-human IgG antibody (Southern Biotech) followed by Sepharose-protein-A or with DNA-cellulose (Pharmacia). The samples were analyzed by SDS-PAGE under reducing conditions. Lane 1, COS-Fab105-Protamine precipitated with anti-human IgG; lane 2, COs-vector precipitated with anti-human IgG and DNA-cellulose; lane 3, COS-Fab105-Protamine precipitated with DNA-cellulose; lane 4 and 5, COS-Fab105 precipitated with DNA-cellulose (4) or with anti-human IgG (5).

The DNA-cellulose coprecipitated the Fd-protamine fusion proteins and Kappa chain, but not the Fab105 fragment, suggesting that the DNA-binding portion cf the Fd-protamine fusion protein maintains its DNA binding ability and the fusion proteins are associated together. The binding activity against HIV gp120, approximately 0.1 µg/ml/24 hours, was detected in the culture medium of COS-Fab105-Protamine cells by enzyme-linked immunosorbent assay (ELISA), while no binding activity was observed in the medium of vector-transformed cells.

Figure 4:
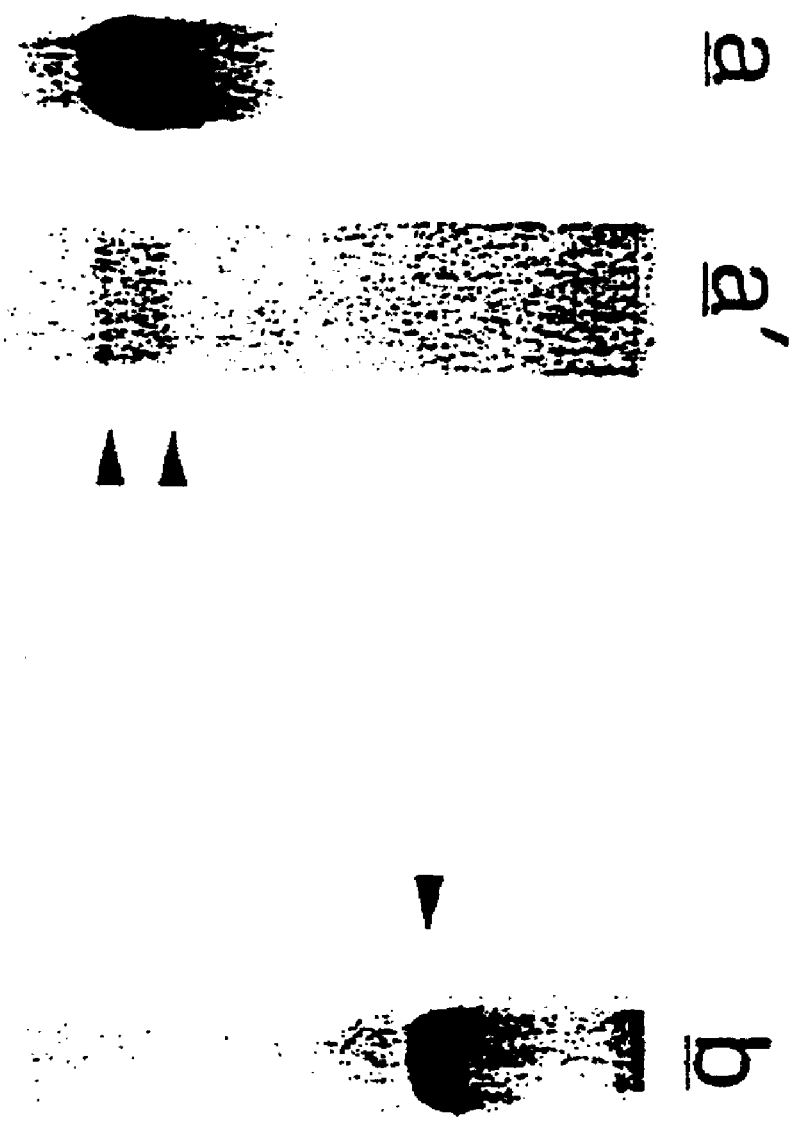
FIG. 4 shows purification and SDS-PAGE analysis of the recombinant fusion proteins.

The secreted recombinant fusion proteins were purified from serum-free culture medium by using an affinity-column coupled with anti-human IgG kappa chain monoclonal antibody (FIG. 4). The fusion proteins bound to the column were eluted by 100 mM glycine (pH 2.4), concentrated and analyzed by SDS-PAGE under nonreducing or reducing conditions following. As shown in FIG. 2, under the reducing condition, two protein bands, corresponding to Fd-protamine fusion protein and kappa chain appeared on the gel. While under non-reducing conditions, the majority of the proteins shifted to a higher molecular weight band, which likely represents assembled Fab fragments. The specific binding activity of the purified Fab105-Protamine to gp120, although slightly lower than that of Fab105, was detected by ELISA.

FIG. 4 shows the purification and SDS-PAGE analysis of the recombinant fusion protein.

The Fab105-Protamine fusion proteins in the culture medium were purified by an affinity-column coupled with anti-human IgG kappa chain monoclonal antibodies (Kirkegaard and Perry Lab) as described. The proteins bound to the column were eluted by 100 mM glycine (pH 2.4) and then concentrated and dialzyed against 0.20 M NaCl solution. The purified proteins were analyzed by SDS-PAGE under reducing or nonreducing conditions following Coomassie blue staining.

Lane a, 100 ng (left), Lane a' 10 ng (right) of purified Fab105-Protamine under the reducing conditions; Lane b 100 ng of purified Fab105-Protamine under non-reducing conditions.

Figure 5:
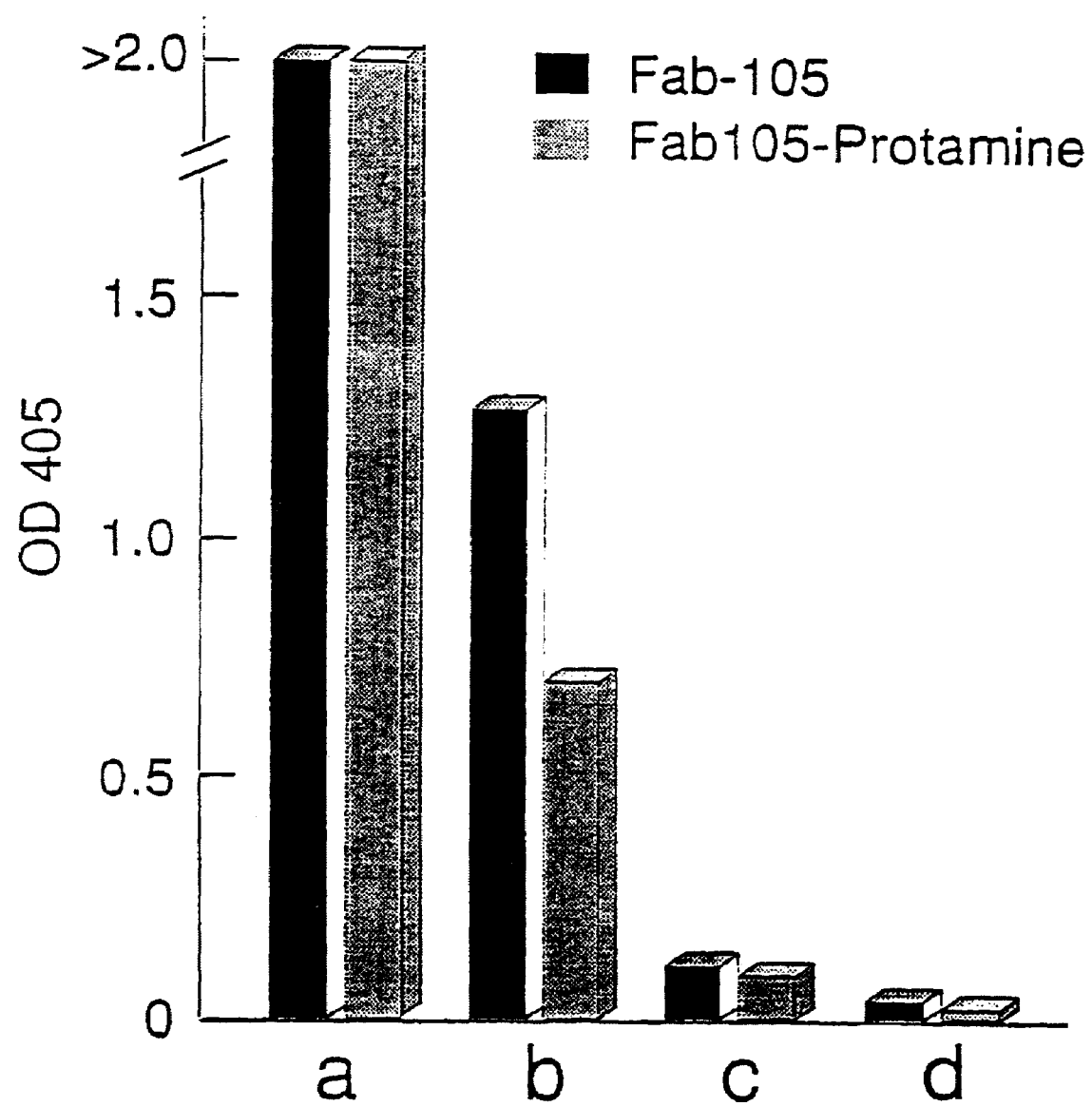
FIG. 5 shows binding activity of the purified fusion proteins to HIV gp120.

Binding activity to Gp120 of the purified fusion protein is shown in FIG. 5.

ELISA plates coated with recombinant HIV-1 gp120 (American Biotechnology, Inc.) were incubated with Fab105 or Fab105-Protamine proteins followed by anti-human IgG conjugated with alkaline phosphatase (Sigma). The binding activity to gp120 was detected at $OD_{405}$ after incubation with substrate (Bio-Lab). The data shown are the mean values from duplicate determination. Lane a, 10 ng/ml of Fab105 or Fab105-protamine; Lane b, 1 ng/ml; Lane c, 0.1 ng/ml and Lane 3, 0.01 ng/ml. The first column in each lane is Fab-105, while the second column is Fab-105-Protamine.

These results indicate that the Fab105-Protamine fusion proteins, which are assembled and secreted into the culture medium, have specific binding activity to HIV-1 gp120.

The DNA binding activity of Fab105-Protamine was examined by a gel-shift assay [Wagner, E., et al., *PNAS USA:*89:6099–6103 (1992)].

DNA Binding Assay

Gel-shift assay was used to analyze the DNA binding activity of the recombinant fusion proteins. The increased amounts of purified fusion proteins in 0.2 N NaCl solution were mixed with a given amount of DNA either radiolabeled or unlabeled in 0.2 N NaCl solution. DNA radiolabelling with $^{32}$P-dATP (Amrasham) was performed using a nick translation kit (Promega). The protein-DNA mixtures was allowed to stand at room temperature for 30 minutes and filtered through 0.45 uM pore-size membrane to eliminate DNA-protein precipitates, and then loaded onto 1.0% agarose gel for electrophoresis at 1×TAE buffer. To analyze cytotoxicity of the DNA-toxin expressor, the fusion protein-DNA mixtures were dialyzed against the normal saline solution at 4° C. overnight before adding to cell cultures.

Figure 6:
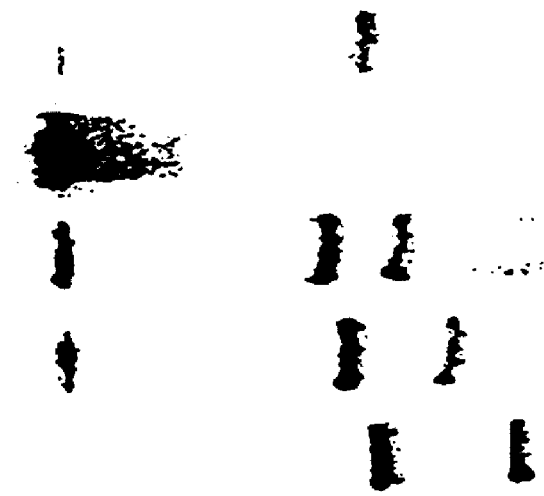
FIG. 6 is an autoradiograph showing the DNA binding activity of the Fab105-protamine fusion proteins under varying concentrations.

The DNA binding activity of Fab105-Protamine protein is shown in FIG. 6.

Figure 7:
FIG. 7 is an autoradiograph showing the DNA binding activity of the Fab105-protamine fusion proteins under varying concentrations.

DNA-binding ability of Fab105-Protamine was examined by gel mobility-shift assay [Wu, G. Y., et al., *J. Biol. Chem.* 262:4429–4432 (1987)]. The HindIII/XbaI-cut DNA fragments of pCMV-Fab105-Protamine was radiolabeled with $^{32}$P-dATP using a nick-translation kit (Pharmacia). 20 ng of labeled DNA for each sample was incubated with increased amount of Fab105-Protamine proteins in 0.20 N NaCl solution. DNA were incubated with Fab105 proteins as control. The whole plasmid DNA pCMV-Fab105-Protamine (0.2 μg each sample) were also incubated with increased amount of pCMV-Fab105-Protamine proteins in 0.20 N NaCl (See, FIG. 7). The samples were analyzed by electrophoresis on 0.8% agarose gels. For autoradiography, the gel was dried, and exposed on X-ray film. FIG. 6: lane 1, DNA (5 ng) only; lanes 2 to 4, DNA (5 ng) with 0.5 ng Fab-Protamine (2); with 1.0 ng Fab-Protamine (3); with 10 ng Fab105-Protamine (4); lane 5, DNA (5 ng)/10 ng Fab105 as control. FIG. 7, lane 1, DNA (0.2 μg) only; lane 2, DNA (0.2 μg)/2.0 μg Fab105 control; lanes 3 to 6, DNA (0.2 μg) with 0.1 μg Fab-Protamine (3); with 0.2 μg Fab-Protamine (4); with 0.4 μg Fab-Protamine (5); with 0.6 μg Fab-Protamine (6), lane 7, Fab105-Protamine only (0.6 μg); and lane 8, DNA (0.2 μg) with 0.6 μg of Fab105-Protamine/phenol extract before loading onto the gel.

As shown in FIGS. 6 and 7, when increasing amounts of the fusion proteins were mixed with the radiolabeled DNA fragments or whole plasmid DNA, the decreasing amounts of DNA fragments or whole plasmid DNA migrated into agarose gels and the DNA entered the agarose gels migrated slower, while the DNA incubated with Fab105 proteins showed no significant change of its mobility in the agarose gels. The binding activity of the fusion proteins to gp120 on the cell surface after coupling with DNA was further examined by fluorescent activated cell sorting (FACS).

Figure 8:
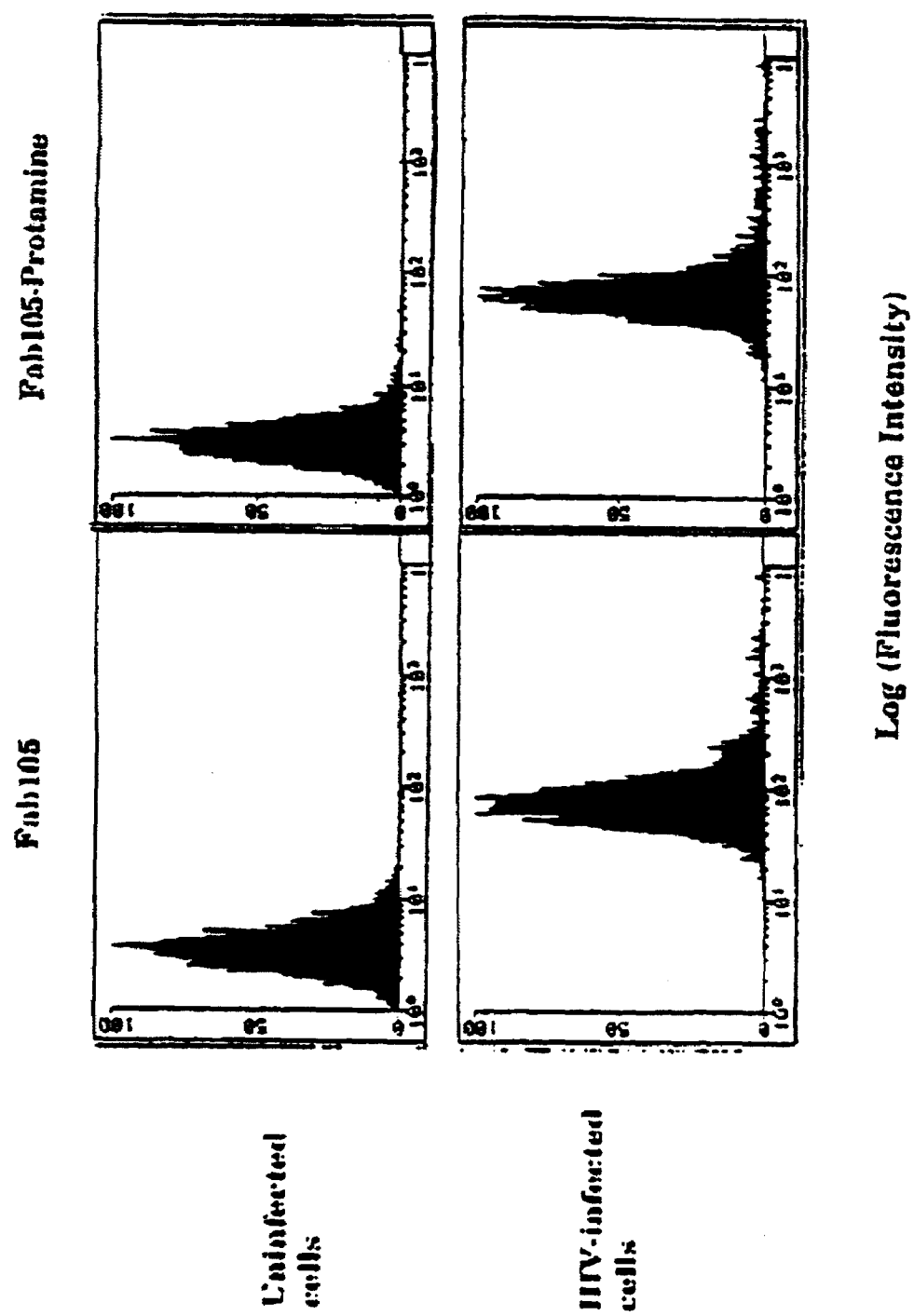
FIG. 8 are FACS analysis showing the binding ability of Fab105-protamine DNA complexes to gp120 protein as compared to that of Fab105 complexes in both uninfected and HIV-infected cells.

Binding ability of Fab105-Protamine-DNA complexes to GP120 on the cell surface is shown in FIG. 8.

The HIV-infected or mock-infected Jurkat cells were incubated with Fab105 or Fab105-Protamine protein-DNA complexes followed by anti-human IgG Fab [Pastan, I., et al., *Science* 254:1173 (1992)] conjugated with Fitc. The fluorescent staining on the cell surface was then analyzed by FACS.

The DNA mobility-shift assay was performed as described [Wu, G. Y., et al., *J. Biol. Chem.* 262:4429 (1987); Wagner, E., et al., *Proc. Natl. Acad. Sci. USA* 89:6099 (1992)]. Increased amounts of purified fusion proteins were mixed with given amounts of DNA in the 0.2 M NaCl solution. The mixtures standed at room temperature for 30 minutes and then filtered through 0.45 μM membrane (Millipore) before loaded onto 0.8% agarose gels for electrophoresis. To detect the binding ability of fusion protein-DNA complexes to gp120 on the cell surface, 1 μg of purified Fab105-Protamine was mixed with 0.5 μg of pCMV-Fab105 plasmid DNA in 100 μl of 0.2 N NaCl for 30 minutes, and the mixtures were diluted to 1:20 at 0.9% N NaCl solution and incubated with HIV-1 infected or uninfected Jurkat cells followed by anti-human IgG-Fitc conjugates. Fab105 fragments were used as a control. The fluorescent staining was then analyzed by FACS.

As shown in FIG. 8, the HIV-1-infected cells reacted with either Fab105 or the Fab105-Protamine-DNA complexes showed positive staining, while uninfected cells incubated with the complexes showed negative staining. The infected cells directly incubated with conjugated antibody also showed negative staining (not shown). Thus, the Fab105-Protamine fusion proteins maintain the binding activity to gp120 after coupling with DNA molecules.

The encoding gene of PEA was selected to construct mammalian toxin expression vectors due to the accumulated knowledge of the encoding gene sequence-function relation [Gary, G. L, et al., *Proc. Natl. Acad. Sci USA*, 81 supra; Allured, V. S., et al., *Proc. Natl. Acad. Sci. USA* 83, supra; Siegall, C. B., et al, *J. Biol. Chem.* 264, supra], PEA has several functional domains: Domain I is responsible for cell recognition: domain II, for translocation of the toxin cross membrane; and domain III, for adenosine diphosphate (ADP)-ribosylation of elongation factor 2, the step actually responsible for cell death [Allured, V. S., *Proc. Natl. Acad. Sci. USA* 83, supra; Siegall, C. B., et al., *J. Biol. Chem.* 264, supra]. Two PEA mammalian expression vectors were designed and constructed in which the domain III (mature PEA amino acid residues of 405 to 613) only (pCMV-PEAIII) or domain III and partial domain Ib sequence (amino acids of 385 to 613) only (pCMV-PEAIb-III) was placed under the control of CMV and T7 promoter.

Construction of Toxin Expression Vectors

Figure 9:
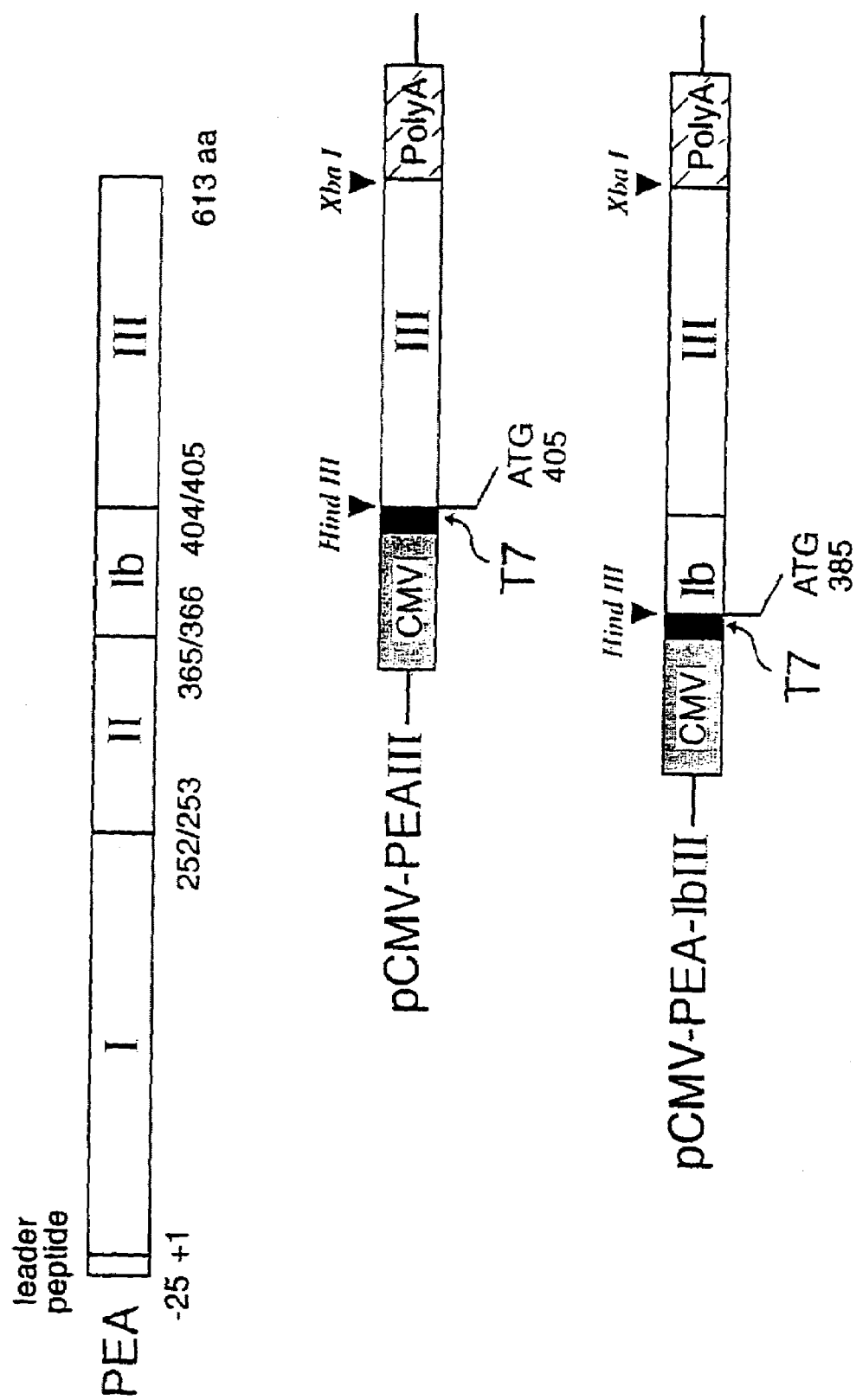
FIG. 9 is a schematic of the expression vectors of the PEA catalytic fragment schematically showing the PEA encoding gene and two vectors made containing partial domains of this gene.
Figure 10:
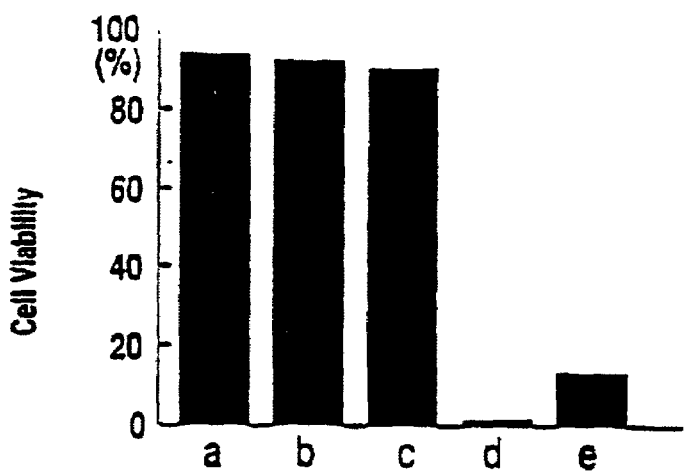
FIG. 10 is a graph showing selective cytotoxicity of one of the nucleic acid delivery systems of the present invention, Fab105-protamine-toxin expressor, to HIV infected cells and shows cell viability.
Figure 11:
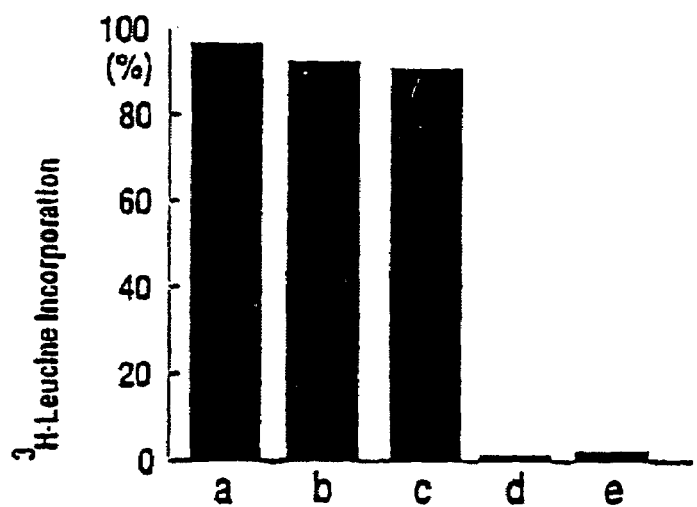
FIG. 11 is a graph showing selective cytotoxicity of Fab105-protamine-toxin expresser complexes to HIV-infected cells and shows a protein inhibition assay.
Figure 12:
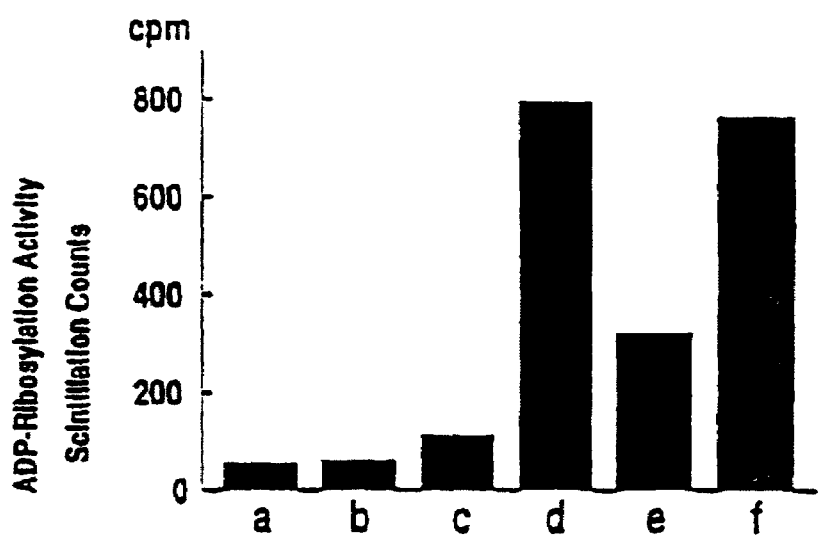
FIG. 12 shows selective cytotoxicity of the Fab105-protamine-toxin expressor complexes to HIV-infected cell as measured by ADP-ribosylation activity.

A plasmid pJH8 containing the PEA encoding gene was obtained from the American Type Culture Collection, 12301 Parklawn Drive, Rockville, Md. 20852, having ATCC Deposit No. 67208. See, FIG. 9 for a schematic showing the PEA encoding domains. The DNA sequences encoding the PEA catalytic fragment were obtained by PCR amplification using pJH8 DNA as a template. To construct the toxin expressor designated as pCMV-PEIII, an upstream primer (P1, (SEQ ID NO:7) 5'TTTAAGCTTATGGGCGACGT-CAGCTTCAGCACC-3') containing an additional HindIII site and an initial codon followed by sequences complimentary to the amino acids 405 to 411 of mature PEA and a downstream primer (P-2, (SEQ ID NO:8) 5'-TTTTCTA-GATTACTTCAGGTCCTCCGG-3') containing the sequence complimentary to amino acids 609 to stop codon of PEA followed by an additional XbaI site were used to amplify domain III of PEA. To construct the toxin expresser pCMV-PEIbIII, an upstream primer (SEQ ID NO:9) (P3–5'-TTTAAGCTTATGGCCGACGTGGTGAGCCTG-3'), corresponding to amino acids 365 to 372 of PEA, and the downstream primer P-2 were used to amplify the partial domain Ib and domain III. The amplified DNA fragments were purified with Geneclean kits (Bio 101 Inc.), digested with HindIII/XbaI and cloned into the pRc/CMV expression vector (Invitrogen) under control of CMV promoter. The resulting constructs were confirmed by DNA sequencing.

These constructs ensure that any expressed toxin fragments without the recognition domain are nontoxic to surrounding cells unless they are expressed inside a cell. To detect the toxin fragments expressed from the vectors, the plasmids pCMV-PEAIII or pCMV-PEAIbIII (See FIG. 9) were first transformed into BL21 (DE3) expression bacterial hosts (Novagen), which inducibly express T7 DNA polymerase for transcription of the gene under the control of T7 promoter. ADP-ribosylation activity was detected from the transformed bacteria after induction (not shown). When the toxin expressors were transfected into mammalian cells (COS-1 and HeLa) using lipofectin [Chen, S. -Y., et al., *J. Virol.* 65:5902–5909 (1991)], toxin fragments were produced and cytotoxicity to the transfected cells was observed (not shown). The pCMV-PEIbIII vector which showed a higher level activity of ADP-ribosylation than pCMV-PEIII was used for further experiments.

To investigate whether Fab105-Protamine can function as a gene carrier to transfer the toxin expressor into target cells, the purified Fab105-protamine fusion proteins were incubated with pCMV-PEAIbIII plasmid DNA at 2:1 ratio (determined by titration) in 0.2 N NaCl solution to form fusion protein-DNA complexes (See FIGS. 10–12). HIV-1-infected Jurkat lymphocytes which were shown over 95% positive by immunofluorescent staining with the antibody against gp120 were used as target cells. The target cells were incubated with the Fab105-Protamine-toxin expressor complexes, toxin expressors only or Fab105-protamine proteins alone. Normal lymphocytes were also incubated with these molecules as control. After 48 hours of incubation, cell viability (FIG. 10), protein synthesis (FIG. 11), and ADP-ribosylation activity (FIG. 12) in the culture cells were examined.

The selective cytotoxicity of Fab105-Protamine-toxin Expressor Complexes to HIV-Infected Cells are shown in FIGS. 10–12.

Jurkat cells were infected with HIV-1 virus and at day 10 postinfection the surface gp120 expression of the cells were examined by immunofluorescent staining. The cells with over 95% gp120 positive ($0.5\times10^6$) were incubated with the DNA-fusion protein complexes, or fusion protein only, or DNA only at 37° C. for 48 hours.

FIG. 10 shows cell viability in the culture examined by Trypan Blue Staining.

Percentage of viable cells were calculated from duplicate determination.

FIG. 11 shows a protein inhibition assay, the cells ($0.5\times10^6$) were replaced with leucine-free medium (See, Allured, V. S., et al., *Proc. Natl, Acad. Sci. USA* 83:1320 (1986); Pastan, I., et al., *Cell* 47:641 (1986); Siegall, C. B., et al., *J. Biol. Chem.* 264:14256 (1989) and added with 4 μci $^3$H-leucine for 4 hours. The cells were centrifuged at 3,000 rpm for 5 minutes and lysed for scintillation counting.

FIG. 12 shows detection of ADP-ribosylation activity in the culture cells [Collier, R. J., et al., *J. Biol. Chem.* 246:1496 (1971)]. The cells ($1\times10^6$) were pelleted by centrifugation and lysed in 4 M urea solution. The supernatants of the lysates were then subjected to the ADP-ribosylation assay and PEA proteins (Gibco-BRL) were used for positive control. The mean scintillation counts of the samples are shown as calculated from duplicate determination.

In FIGS. 10–12 lane a: normal Jurkat cells incubated with Fab-Protamine-toxin expressor complexes (10 μg Fab105-Protamine/5 μg expressor DNA, 10:5 μg); lanes b to e: HIV-infected Jurkat cells incubated with Fab-Protamine only (b); with toxin expressor DNA only (C); with Fab105-Protamine-Toxin expressor complexes (10:5 μg) (d); with Fab105-Protamine-toxin expressor complexes (5:2.5 μg) (e); lane f:ADP-ribisylation activity of 1.0 ng of urea-denatured PEA control.

As shown in FIGS. 10–12, after incubation with Fab105-Protamine-toxin expressor complexes for 48 hours, the HIV-1-infected cells showed a significant decrease of cell viability (<1.5%) and protein synthesis ability (<0.2%); while the cells incubated with toxin expressor or Fab105-protamine alone only showed slightly decreased cell viability and protein synthesis ability. In addition, uninfected lymphocytes showed no significant decreases of cell viability and protein synthesis ability after incubation with the Fab105-Protamine-toxin expressor complexes. The observed selective cytotoxicity to HIV-infected cells should be a result of ADP-ribosylation activity from expressed toxin fragments since ADP-ribosylation activity, roughly equal to 1.0 ng of PEA proteins, was detected from lysates of the HIV-infected cells ($1\times10^6$) incubated with the complexes. Thus, the Fab105-Protamine-toxin expressor complexes selectively intoxicate HIV-1 infected cells in tissue culture.

A major obstacle of immunotoxins as efficacious agents in the treatment of human cancer and other diseases is the host antibody response to xenogeneic antibodies and toxin molecules.[Byers, V. S., et al., *Immunol.* 65:329 (1988); Durrant, L. G., et al., *Clin. Exp. Immunol.* 75:258 (1989); Pai, L. H., et al., *J. Clin. Oncol.* 9:2095–2103 (1991)]. The utilization of humanized murine or human antibodies may solve the problem of targeting moiety [Rybak, S. M., et al., *Proc. Natl. Acad. Sci. USA* 89:3165–3169 (1992)], but for highly immunogenic toxin moiety, the problem still remains. In this study we demonstrate that the anti-gp120 Fab105-Protamine fusion proteins can serve as a gene carrier to deliver toxin-expressor plasmid DNAs into HIV-1-infected cells by receptor-mediated endocytosis, resulting in selective killing of the target cells. The extreme potency of the toxin molecules compensates for the low efficiency of the receptor-mediated gene delivery [Wu, G. Y., et al., *J. Biol. Chem.* 262: 4429–4432 (1987); Wagner, E., et al., *PNAS USA*

89:6099–6103 (1992)] to efficiently achieve the therapeutic goal. Since that antibody molecules or ligands (targeting moiety) and DNA-binding moiety of bifunctional fusion proteins can be of human origin, and the toxin expressor DNAs are very weakly or non immunogenic, the whole protein-toxin expressor complexes will be weakly immunogenic. Therefore, these complexes should be able to be repeatedly administered into patients without development of significant antibody response. Furthermore, the bifunctional recombinant fusion proteins as a gene carrier also have the advantage over chemically linked ones [Wu, G. Y., et al., *J. Biol. Chem.* 262:4429–4432 (1987); Wagner, E., et al., *PNAS USA* 89:6099–6103 (1992)], such as efficient production, and potentially better binding activity. In summary, this gene therapy form of immunotoxins, termed herein "stealth immunotoxins" has significant advantages over currently described immunotoxins for treatment of cancers, and other diseases. Moreover, the anti-gp120 Fab105-Protamine-toxin expresser complexes have selective toxicity to HIV-1-infected cells which also represent a novel therapeutic agent for AIDS treatment.

All references described herein are incorporated herein by reference.

It is evident that those skilled in the art given the benefit of the foregoing disclosure may make numerous other uses and modifications thereof and departures from the specific embodiments described herein without departing from the inventive concepts, and the present invention is to be limited solely by the scope and spirit of the appended claims.

We claim:

1. A nucleic acid delivery system comprising:

(1) a fusion protein, wherein said fusion protein is prepared by recombinant techniques and contains:

(a) an antibody targeting moiety, which will specifically bind to a site on a target cell, and (b) a binding moiety which will bind to a nucleic acid segment, and (2) a nucleic acid sequence comprising the nucleic acid segment and a nucleic acid sequence of interest, wherein the fusion protein is encoded by a nucleic acid having no stop codon between the antibody targeting moiety encoding nucleic acid segment and the nucleic acid segment encoding the binding moiety which will bind to a nucleic acid segment.

2. The nucleic acid delivery system of claim 1, wherein the binding moiety is a protein or the nucleic acid binding domain of a protein, and the binding moiety is fused to the carboxy portion of the targeting moiety.

3. The nucleic acid delivery system of claim 2, wherein the binding moiety is the protein protamine.

4. A nucleic acid delivery system comprising a fusion protein wherein one portion of the fusion protein comprises an antibody, which will selectively bind to a desired site on a cell, and the other portion of the fusion protein comprises a protarnine protein capable of binding to a nucleic acid segment; and the nucleic acid segment.

5. The nucleic acid delivery system of claim 4, wherein the nucleic acid segment is a DNA sequence corresponding to a cytotoxin gene or a fragment thereof which will encode a cytotoxic protein.

6. The nucleic acid delivery system of claim 5, wherein the nucleic acid segment encodes at least Domain III of *Pseudomonas exotoxin* A.

7. A method of use of a nucleic acid delivery system which comprises administering an effective amount of the nucleic acid delivery system of claim 4 to serum containing a target cell, and contacting the target cell with the nucleic acid delivery system, whereby the target cell is transfected with the nucleic acid sequence.

8. A nucleic acid delivery system comprising:
(1) a fusion protein, wherein said fusion protein is prepared by recombinant techniques and contains:
   (a) an antibody targeting moiety, which will specifically bind to a site on a target cell, wherein the antibody is an antibody to a viral envelope protein, a cellular receptor, or an extracellular domain of an activated receptor, and
   (b) a binding moiety which will bind to a nucleic acid segment, and
(2) a nucleic acid sequence comprising the nucleic acid segment and a nucleic acid sequence of interest.

9. The nucleic acid delivery system of claim 8, wherein the antibody is to a viral envelope protein.

10. A nucleic acid delivery system comprising:
(1) a fusion protein, wherein said fusion protein is prepared by recombinant techniques and contains:
   (a) an antibody targeting moiety, which will specifically bind to a site on a target cell, wherein the antibody is a single chain antibody, a Fab portion of an antibody, or a (Fab')$_2$ segment and
   (b) a binding moiety which will bind to a nucleic acid segment, and
(2) a nucleic acid sequence comprising the nucleic acid segment and a nucleic acid sequence of interest.

11. The nucleic acid delivery system of claim 8 or 10, wherein the nucleic acid sequence of interest encodes an antibody, a dominant negative mutant, an antisense RNA, ribozymes, or a cytotoxic agent.

12. The nucleic acid delivery system of claim 8 or 10, wherein the nucleic acid segment comprises a promoter operably linked to a desired gene in the nucleic acid sequence of interest, wherein said promoter and gene are flanked by 5' and 3' long terminal repeat (LTR) regions or inverted terminal repeat (ITR) regions.

13. A method of transforming a target cell which comprises adding an effective amount of the nucleic acid delivery system of claim 8 or 10 to a medium containing the target cell, and contacting the target cell with the nucleic acid delivery system, whereby the target cell is transfected with the nucleic acid sequence.

14. The method of claim 13, wherein the nucleic acid sequence is RNA.

15. A method of preparing a nucleic acid delivery system which comprises transforming a cell with a vector containing a DNA segment which encodes the fusion protein of claim 8 or 10 operably linked to a promoter, incubating the cell, and collecting the expressed fusion protein.

16. A method of use of a nucleic acid delivery system which comprises administering an effective amount of the nucleic acid delivery system of claim 8 or 10 to serum containing a target cell, and contacting the target cell with the nucleic acid delivery system, whereby the target cell is transfected with the nucleic acid sequence.

17. The method of claim 16, wherein the nucleic acid sequence is RNA.

18. A method of transforming a target cell in vivo with RNA which comprises administering the nucleic acid delivery system of claim 8 or 10 to a subject containing the target cell, wherein the nucleic acid sequence is RNA.

* * * * *

```
                         SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
          (A) LENGTH: 8 amino acids
          (B) TYPE: amino acid
          (C) STRANDEDNESS: unknown
          (D) TOPOLOGY: unknown (xi) SEQUENCE DESCRIPTION: SEQ ID NO:1:

Lys Lys Lys Tyr Tyr Lys Leu Lys
1               5

(2) INFORMATION FOR SEQ ID NO:2:

(i) SEQUENCE CHARACTERISTICS:
          (A) LENGTH: 36 base pairs
          (B) TYPE: nucleic acid
          (C) STRANDEDNESS: unknown
          (D) TOPOLOGY: unknown (xi) SEQUENCE DESCRIPTION: SEQ ID NO:2:

TTTGAATTCA AGCTTACCAT GGAACATCTG TGGTTC                                 36

(2) INFORMATION FOR SEQ ID NO:3:

(i) SEQUENCE CHARACTERISTICS:
          (A) LENGTH: 33 base pairs
          (B) TYPE: nucleic acid
          (C) STRANDEDNESS: unknown
          (D) TOPOLOGY: unknown (xi) SEQUENCE DESCRIPTION: SEQ ID NO:3:

GGTACCGAAT TCTCTAGAAC AAGATTTGGG CTC                                    33

(2) INFORMATION FOR SEQ ID NO:4:

(i) SEQUENCE CHARACTERISTICS:
          (A) LENGTH: 36 base pairs
          (B) TYPE: nucleic acid
          (C) STRANDEDNESS: unknown
          (D) TOPOLOGY: unknown (xi) SEQUENCE DESCRIPTION: SEQ ID NO:4:

GGTACCGAAT TCTCTAGAAT GGCCAGGTAC AGATGC                                 36
```

(2) INFORMATION FOR SEQ ID NO:5:

(i) SEQUENCE CHARACTERISTICS:
        (A) LENGTH: 48 base pairs
        (B) TYPE: nucleic acid
        (C) STRANDEDNESS: unknown
        (D) TOPOLOGY: unknown (xi) SEQUENCE DESCRIPTION: SEQ ID NO:5:

```
TTTAGGATCC TTAACAACAC CTCATGGCTC TCCTCCGTGT CTGGCAGC                48
```

(2) INFORMATION FOR SEQ ID NO:6:

(i) SEQUENCE CHARACTERISTICS:
        (A) LENGTH: 78 base pairs
        (B) TYPE: nucleic acid
        (C) STRANDEDNESS: unknown
        (D) TOPOLOGY: unknown (xi) SEQUENCE DESCRIPTION: SEQ ID NO:6:

```
TTAATTGCGG CCGCTTAGTG TCTTCTACAT CTCGGTCTGT ACCTGGGGCT GACACCTCAT    60

GGCTCTCCTC CGTGTCTG                                                 78
```

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO:7:

```
TTTAAGCTTA TGGGCGACGT CAGCTTCAGC ACC                                33
```

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (xi) SEQUENCE DESCRIPTION: SEQ ID NO:8:

```
TTTTCTAGAT TACTTCAGGT CCTCCGG                                       27
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (xi) SEQUENCE DESCRIPTION: SEQ ID NO:9:

```
TTTAAGCTTA TGGCCGACGT GGTGAGCCTG                                    30
```